United States Patent
Cohen et al.

(10) Patent No.: US 7,627,334 B2
(45) Date of Patent: Dec. 1, 2009

(54) SYSTEMS AND METHODS FOR CONTEXT RELEVANT INFORMATION MANAGEMENT AND DISPLAY

(75) Inventors: Mark Cohen, Atlanta, GA (US); Jane Cohen, Atlanta, GA (US)

(73) Assignee: Contextual Information, Inc., Atlanta, GA (US)

( * ) Notice: Subject to any disclaimer, the term of this patent is extended or adjusted under 35 U.S.C. 154(b) by 1045 days.

(21) Appl. No.: 10/768,356

(22) Filed: Jan. 30, 2004

(65) Prior Publication Data

US 2005/0021369 A1   Jan. 27, 2005

Related U.S. Application Data

(60) Provisional application No. 60/489,040, filed on Jul. 21, 2003.

(51) Int. Cl.
*H04W 24/00* (2009.01)
*G06Q 10/00* (2006.01)
*G06Q 50/00* (2006.01)
*G06F 19/00* (2006.01)
*A61B 5/00* (2006.01)

(52) U.S. Cl. .................... 455/456.3; 455/456.1; 705/2; 705/3

(58) Field of Classification Search .............. 455/456.3, 455/456.1; 705/2, 3
See application file for complete search history.

(56) References Cited

U.S. PATENT DOCUMENTS

| | | | |
|---|---|---|---|
| 4,857,716 A | 8/1989 | Gombrich et al. | 235/462 |
| 4,916,441 A | 4/1990 | Gombrich | 340/712 |
| 5,602,963 A | 2/1997 | Bissonnette et al. | 395/2.84 |
| 5,682,142 A | 10/1997 | Loosmore et al. | 340/572 |
| 5,737,539 A | 4/1998 | Edelson et al. | 395/203 |
| 5,822,544 A | 10/1998 | Chaco et al. | 395/202 |
| 5,825,149 A * | 10/1998 | Matsumoto et al. | 318/587 |
| 5,960,085 A * | 9/1999 | de la Huerga | 340/5.61 |
| 5,971,931 A | 10/1999 | Raff | 600/485 |
| 5,991,730 A | 11/1999 | Lubin et al. | 705/3 |
| 6,057,758 A | 5/2000 | Dempsey et al. | 340/539 |
| 6,091,956 A * | 7/2000 | Hollenberg | 455/456.5 |
| 6,272,347 B1 | 8/2001 | Griffith et al. | 455/445 |
| 6,281,841 B1 | 8/2001 | Nevill | 342/424 |

(Continued)

OTHER PUBLICATIONS

R. Neame, "Networking Care: the Information Management Perspective," (6 pages). No date provided.

M.N. Kamel Boulos, "Location-based health information services: a new paradigm in personalized information delivery," International Journal of Health Geographics 2003; 2(1):2.

G.T. Huang, "less Sensor Net," Technology Review, pp. 51-56, Jul./Aug. 2003.

(Continued)

*Primary Examiner*—Rafael Pérez-Gutiérrez
*Assistant Examiner*—Allahyar Kasraian
(74) *Attorney, Agent, or Firm*—Sutherland Asbill & Brennan LLP

(57) ABSTRACT

A wireless information device provides a user with context relevant information. The precise location of the wireless device is monitored by a tracking system. Using the location of the wireless device and the identity of the user, context relevant information is transmitted to the device, where the context relevant information is pre-defined, at least in part, by the user. Context relevant information served to the device depends on the identity of the user, the location of the device, and the proximity of the device to persons or objects. The wireless information device may be used by healthcare workers, such as physicians, in hospitals, although other environments are contemplated, such as hotels, airports, zoos, theme parks, and the like.

26 Claims, 16 Drawing Sheets

U.S. PATENT DOCUMENTS

| | | | |
|---|---|---|---|
| 6,327,570 | B1 | 12/2001 | Stevens .......................... 705/7 |
| 6,347,329 | B1 | 2/2002 | Evans ........................ 709/202 |
| 6,353,398 | B1* | 3/2002 | Amin et al. ............ 340/995.12 |
| 6,364,834 | B1* | 4/2002 | Reuss et al. ................. 600/300 |
| 6,408,330 | B1 | 6/2002 | DeLaHuerga ............... 709/217 |
| 6,459,989 | B1 | 10/2002 | Kirkpatrick et al. .......... 701/215 |
| 6,587,835 | B1 | 7/2003 | Treyz et al. .................... 705/14 |
| 6,591,242 | B1* | 7/2003 | Karp et al. ..................... 705/2 |
| 7,357,308 | B2* | 4/2008 | Matz .......................... 235/380 |
| 7,421,466 | B2* | 9/2008 | Haines ........................ 709/200 |
| 2001/0056359 | A1* | 12/2001 | Abreu ............................ 705/3 |
| 2002/0002504 | A1 | 1/2002 | Engel et al. ................... 705/26 |
| 2002/0016719 | A1 | 2/2002 | Nemeth et al. ................. 705/2 |
| 2002/0035484 | A1 | 3/2002 | Mccormick .................... 705/2 |
| 2002/0055855 | A1 | 5/2002 | Cule et al. ..................... 705/2 |
| 2002/0107715 | A1 | 8/2002 | Pace et al. ..................... 705/8 |
| 2002/0116219 | A1 | 8/2002 | Ibok et al. ...................... 705/2 |
| 2002/0120472 | A1 | 8/2002 | Dvorak et al. .................. 705/3 |
| 2002/0128872 | A1 | 9/2002 | Giammattei ................... 705/3 |
| 2002/0147615 | A1 | 10/2002 | Doerr et al. .................... 705/2 |
| 2002/0165733 | A1 | 11/2002 | Pulkkinen et al. .............. 705/2 |
| 2002/0198473 | A1 | 12/2002 | Kumar et al. ............... 600/595 |
| 2003/0043073 | A1 | 3/2003 | Gray et al. .................. 342/465 |
| 2003/0055707 | A1 | 3/2003 | Busche et al. ................ 705/10 |
| 2003/0078911 | A1 | 4/2003 | Haskell et al. ................. 707/2 |
| 2003/0083903 | A1* | 5/2003 | Myers ........................... 705/2 |
| 2003/0144710 | A1 | 7/2003 | Pless et al. ................... 607/60 |
| 2003/0144874 | A1 | 7/2003 | Barret et al. ................... 705/2 |
| 2003/1014092 | * | 7/2003 | Wilkes et al. ............... 128/898 |
| 2004/0010425 | A1* | 1/2004 | Wilkes et al. .................. 705/3 |
| 2004/0078231 | A1* | 4/2004 | Wilkes et al. .................. 705/2 |
| 2004/0128163 | A1* | 7/2004 | Goodman et al. .............. 705/2 |
| 2004/0167465 | A1* | 8/2004 | Mihai et al. .................. 604/67 |
| 2004/0172300 | A1* | 9/2004 | Mihai et al. .................... 705/2 |
| 2004/0172301 | A1* | 9/2004 | Mihai et al. .................... 705/2 |
| 2004/0172302 | A1* | 9/2004 | Martucci et al. ............... 705/2 |
| 2004/0176667 | A1* | 9/2004 | Mihai et al. ................. 600/300 |
| 2004/0176983 | A1* | 9/2004 | Birkett et al. .................. 705/2 |
| 2004/0193449 | A1* | 9/2004 | Wildman et al. ............... 705/2 |
| 2004/0203897 | A1* | 10/2004 | Rogers .................... 455/456.1 |
| 2004/1020406 | * | 10/2004 | Van Erlach .............. 455/556.1 |
| 2004/0254816 | A1* | 12/2004 | Myers ........................... 705/2 |
| 2004/0263319 | A1* | 12/2004 | Huomo ..................... 340/10.2 |
| 2005/0055242 | A1* | 3/2005 | Bello et al. .................... 705/2 |
| 2005/0055244 | A1* | 3/2005 | Mullan et al. .................. 705/2 |
| 2005/0065817 | A1* | 3/2005 | Mihai et al. .................... 705/2 |
| 2005/0136947 | A1* | 6/2005 | Llombart-Juan et al. . 455/456.3 |
| 2005/0258957 | A1* | 11/2005 | Krumm et al. ......... 340/539.13 |
| 2006/0053036 | A1* | 3/2006 | Coffman et al. ................ 705/2 |

OTHER PUBLICATIONS

M. Vandre, "Help for Handhelds, Interfaces" Technology Review, p. 26, Jul./Aug. 2003.

D. Talbot, "Fixing the Location Fix, Ten-centimeter GPS resolution is quite close to be here," Technology Review, p. 26, May 2003.

Technical Applications of Our Current Technology, (4 pages). No date provided.

D.W. Bates and A. A. Gawande, "Improving Safety With Information Technology," N Eng J Med 2003; 348:2526-34.

M. Mankins, "Location Linked Information: a framework for emergent, location-based content deployment," Massachusetts Institute of Technology, (9 pages) Fall 2002.

F.J. Overdyk, G.R. Haynes, and P.J. Arvanitis, "Patient-Borne Memory Device Facilitates "Point of Care" Data Access," MD Computing, pp. 60-63, May/Jun. 1999.

J. Carrier, "A Stroll Through the Ivy, With a Tour Guide That Beeps," New York Times, Aug. 21, 2003.

R. Zacks, "O.R. of the Future," Technology Review, pp. 73-75, Sep. 2003.

J. Jackson, "Brainy Radio, Researchers tune in on wireless devices that learn," Technology Review, p. 28, Feb. 2003.

E.W. Pfeiffer, "WhereWare," Technology Review, pp. 46-52, Sep. 2003.

"An Ultrawideband Who's Who," Technology Review, p. 79, Sep. 2002.

Millennial Net, Wireless Sensor Networking Anywhere, 2003.

Versus Technology, Inc., When Location is Everything, www.versustech.com, May 30, 2002.

Pulse~Link, Inc. Home Page—Technology, (2 pages), San Diego, CA, 2001.

WhereNet Company Overview; www.wherenet.com, May 4, 2002.

H. Stewart Cobb, "GPS Pseudolites: Theory, Design, and Applications," Sep. 1997.

T. J. Fitzgerald, "Cart 54, Where Are You? The Tracking System Knows," The New York Times, Oct. 30, 2003.

J. Goedert, "Mobile Clinical Apps: The Race is On," Health Data Management, Oct. 1, 2003.

* cited by examiner

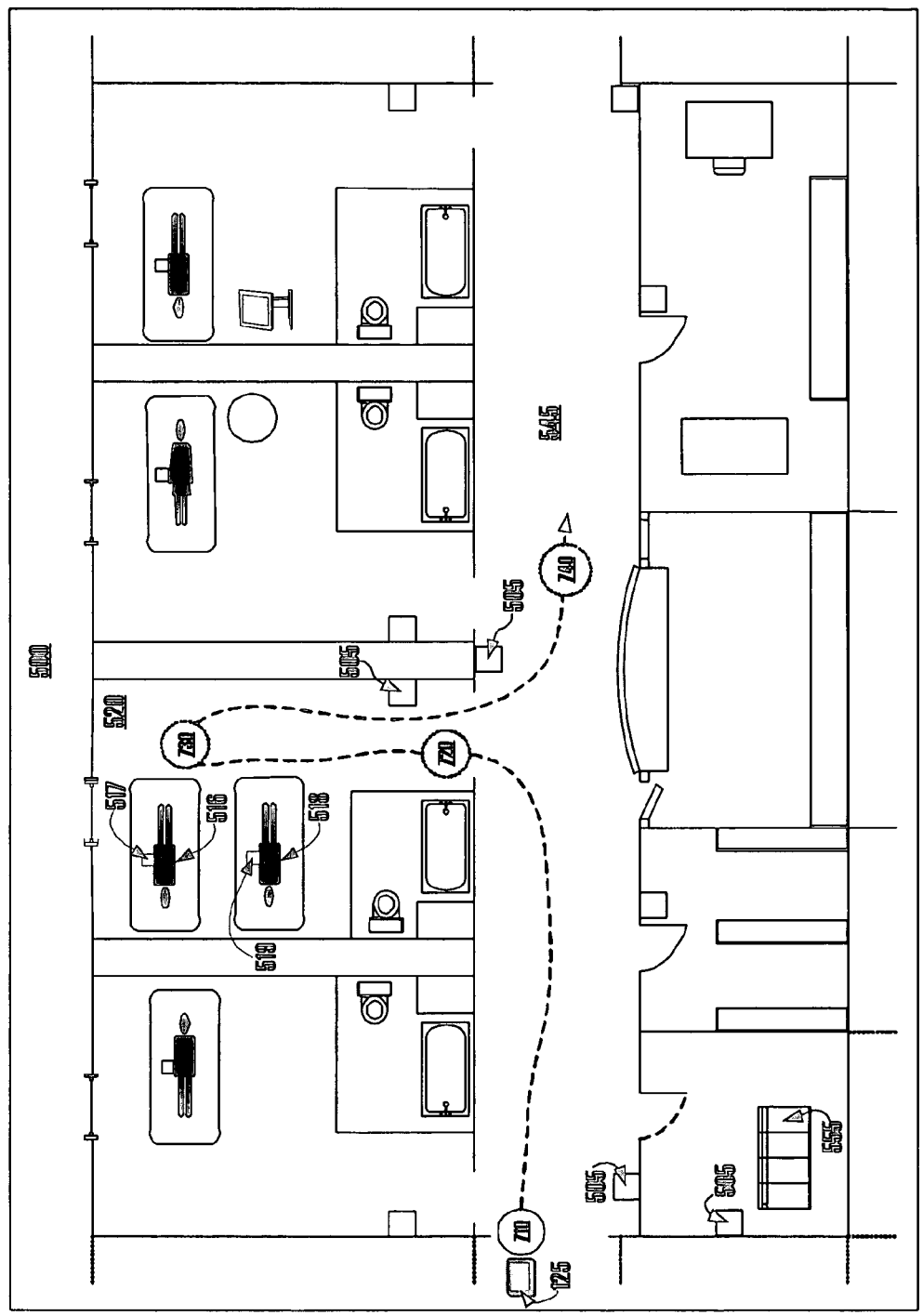

SYSTEMS AND METHODS FOR CONTEXT RELEVANT INFORMATION MANAGEMENT AND DISPLAY

RELATED APPLICATION DATA

The present application claims the benefit of U.S. Provisional Patent Application Ser. No. 60/489,040, filed Jul. 21, 2003, titled "Systems And Methods for Automatic Data Retrieval And Presentation Based At Least In Part On User Context", which is hereby incorporated by reference as if set forth fully herein.

FIELD OF THE INVENTION

The present invention relates to systems and methods for delivery and interaction with information based on context, and more specifically, to wireless information management and display based on a user's identity, location, and proximity to other location-identified devices, objects, and users.

BACKGROUND OF THE INVENTION

The information age has resulted in an explosion of the amount of information that can be brought to bear in problem management. The connections among the ever increasing volume of relevant information have resulted in a near chronic state of information overload for all but the most trivial of situations. As decision managers are deluged by this overwhelming flood of information, they lose their ability to manage the details and connections of the relevant information. The end result is error laden uninformed sub-optimal decisions.

Designers of computer based data delivery systems have traditionally been reluctant to make decisions about selective presentation of data out of fear of leaving out relevant and important information. This fear is real, because the context in which the user is using the information is not known. The response to this concern has been for the system designers to present all possible information, usually in long lists with no connection from one item to the next. The designer is deliberately leaving the filtering and association building to the user.

People compensate for information overload in many ways. All are attempts to reduce an overwhelming volume of information to an amount that can be assimilated in the context of the problem to be solved. If the amount of information presented is overwhelming and unorganized, then volumes of data are filtered, and only isolated data points incorporated into one's thinking. Presenting large amounts of information not relevant to the decision at hand creates "noise" and the important information is drowned out. This only compounds confusion, contributes to poor decision making, and impedes the decision making process.

When relevant data is missing, users have an equally difficult problem. If the fact that information is missing is not identified, an uninformed decision results. If the relevant data is known to exist, but is not available, the user must decide whether to track down the information. The typical strategy is to "do the best I can" with the limited information presented. Additional data that are not presented, but could be brought to bear on the decision process, are ignored; the effort to locate the data is too great at the moment. Error laden poor decisions result.

When information is created, it must be presented to the user of the information. People have a limited capacity to form and remember associations. Therefore, information presented out of context is generally either ignored or forgotten. The designers of the computer systems that manage information are faced with the impossible design decision of either having the computer withhold information, or present it at the time it is created. Because the computer system does not know anything about the location of the user, nor what the user is attempting to do, there is no ability to incorporate the context of a situation into the decision about the delivery of the data. This delivery of data irrelevant to the decision at hand, ensures that the information will not be available later, when it is needed.

Health care in a hospital is a prototypic environment that has been overcome by information overload. The explosion of health care technology has resulted in a massive increase in the amount of information generated about a patient. In caring for a critically ill patient in an intensive care unit, hundreds of individual data points can be created daily. Information is spread among various locations and systems. No health care worker is able to track down all the data items, assimilate the information, make the translation to knowledge, and create a decision. The error rate in health care delivery has increased exponentially. Tens of thousands of deaths per year are felt due to errors in the implementation of testing and therapies in hospitals. The technicians, doctors, and nurses are unable to manage the details of diagnosis, treatment, medicine interactions, collection of test results, and communication. They compensate by trying to remember details, but the limitations of memory are overwhelmed. In general, the information that is selectively ignored exists in the hospital information systems, but is not easily accessible at the time the care is delivered, or is buried in a mountain of irrelevant information.

Therefore, it will be appreciated that for information to be useful, it must be presented in context. Only the data that applies to the current decision maker, the current patient, and the current care to be delivered is relevant. All other information must be suppressed. It is not sufficient for the information to exist, but to not be obtainable. It is not sufficient for the information to be scattered over many different computer systems or recording media (paper, X-Ray film, telephone). All the information must be brought to the hands and eyes of the caregiver at the exact moment it is needed, and only that information can be presented. Even having the computer screen out of the hands of the healthcare worker will defeat the ability of the contextually relevant information to guide the correct decisions.

Healthcare is not the only environment in which information overload, irrelevance, and inaccessibility inhibits effective data management and decision making. In a hotel, customers all have specific and idiosyncratic needs that are in a perpetual state of flux. The staff attempt to anticipate and respond to requests. Coordinating the people and resources in the hotel is expensive and inefficient. If the customer needs could be presented to the staff in a manner relevant to the context of the situation, this process could be improved.

Presentation of information, even when decision making is not involved, is difficult in the age of information overload. An example in which it is difficult to present situation-relevant information is a large zoo with open habitats. Information sources are fixed, such as a display at a habitat overlook, or uniform, such as from a guide book. That the animals being viewed are mobile, and the educational levels of the viewers are disparate, is ignored. As a result, the PhD Zoologist and the 8 year old on a school trip are presented the same information about an animal: even if that animal is not visible at the time. If the information displayed were to be targeted to the level of each viewer, and only information about animals in view was presented, the experience of each viewer would be enhanced.

Thus, there exists a unsatisfied need in the industry for the management and display of context relevant information. It would be advantageous if a user could receive context relevant information, where the context relevant information is based on the user's identity, the user's physical location, and the user's proximity to other people and objects. Furthermore, it would be advantageous if such information were delivered to users in a form such that information important to each user is immediately available without requiring users to navigate through multiple documents, pages or screens.

SUMMARY OF THE INVENTION

This present invention allows for the management of information based on context and relevance. The term context, as used herein, is the intersection of the user's identity, the user's physical location, and the user's proximity to other people and objects. Therefore, context relevant information is information that is based on a user's identity, physical location, and proximity to other persons and objects. The present invention uses information displays to provide context relevant information.

According to one aspect of the invention, the physical location of information displays are known to high spatial resolution. These displays may be of any type: data tablets, laptop computers, handheld digital assistants (PDA's), cell phone displays, or fixed workstations. The physical geographic location of people, equipment, and computers are also known with high spatial resolution. The location system may be based on any number of technologies, including global positioning satellites (GPS) with correction, local wireless, infrared, or manually input, such as barcode. The identity of the user of the system is known via direct input, smart card, RF tag, or biometric input. Information to be managed resides in a central computer system.

The present invention uses context to assist in the management of information. More specifically, information relevance is determined by context. Out of the nearly limitless amount of information that can be displayed and managed, only the contextually relevant information is displayed. This solves the problems created when users are overwhelmed by the amount of information presented. Similarly, this invention facilitates the display of immediately important information, avoiding the problem of relevant information being pushed out of view by irrelevant information.

The user's identity allows the display of information to be tailored automatically to the specific needs of the user. In an identical situation, with proximity to identical people and objects, information relevant to one user will be different from that relevant to another. As the users move through their environment, and objects move in and out of proximity to the users, the data display automatically adjusts to be continually displaying only contextually relevant information.

When users are presented with only contextually relevant information, decision making and implementation becomes straightforward. Users do not have to rely only on their memories to acquire information. Ancillary data is presented at the exact moment it is needed. Decisions become clear and error rates are dramatically reduced.

According to one embodiment of the present invention, there is disclosed a method for serving context-relevant information. The method includes identifying a user associated with a wireless information device (WID), determining the location of the WID, and ascertaining the proximity of the WID to at least one object. The method also includes transmitting context-relevant content to the WID, where the context-relevant content is based at least in part on the identity of the user, the location of the WID, and the proximity of the WID to the at least one object.

According to one aspect of the invention, the step of identifying a user includes identifying the user based on a device associated with the user. The device may be a smart card, radio frequency tag, infrared tag, or barcode. According to another aspect of the invention, the user is identified via user based on biomedical indicia. The at least one object near the WID may be a person, such as a patient, equipment (e.g., hospital equipment), animal, or any other moveable object. According to yet another aspect of the invention, the context-relevant information is presented to the user via a WID display. The step of presenting the context-relevant information may also include the step of presenting the context-relevant information to the user based on display rules established, at least in part, by the user.

According to another aspect of the invention, the display rules may be stored external to the WID. The method may also include the steps of receiving user-input information at the WID, and transmitting the user-input information to a server, e.g., a computer server. According to one aspect of the invention, the location of the WID may be determined using a tracking system such as a global positioning system (GPS) or radio frequency-based positioning system. Further, the step of ascertaining the proximity of the WID to at least one object may include the step of determining the distance of the WID to the at least one object.

According to another embodiment of the invention, there is disclosed a method for receiving information at a device. The method includes the step of identifying a user associated with a WID and accessing information rules associated with the user, where the information rules establish the type of content transmitted to the WID. The method also includes the step of transmitting context relevant information to the WID, where the context relevant information is identified based at least in part on the information rules, the identity of the user, and the identity of a person or object located near the WID.

According to one aspect of the invention, the information rules are established, at least in part, by the user. According to another aspect of the invention, the step of accessing information rules includes the step of accessing information rules stored remote from the WID. The information rules may also define the arrangement in which the context relevant information is displayed on the WID. According to yet another aspect of the invention, the method may further include the step of receiving information transmitted from the WID.

The step of accessing information rules may include accessing information rules defining the content and format of context relevant information transmitted to the WID. Additionally, the step of identifying a user may include identifying the user based on a device associated with the user. According to another aspect of the invention, the device is a smart card, radio frequency tag, infrared tag, or barcode. According to yet another aspect of the invention, the step of identifying the user includes identifying the user based on biomedical indicia of the user.

According to yet another embodiment of the invention, there is disclosed a system for displaying information. The system includes an information device associated with a user and at least one server, in wireless communication with the information device, where the at least one server is operable to transmit context relevant information to the information device. In the system the context-relevant information is based at least in part on the identity of the user, the location of the WID, and the proximity of the WID to at least one object.

According to one aspect of the invention, the system also includes at least one database in communication with the at least one server, where the at least one database is operable to store information from which the context relevant information is retrieved. The at least one server may also be associated with a facility. The at least one database may include a hospital database that stores patient information, or a database external to the hospital. According to another aspect of the invention, the context relevant information includes patient information.

The system may also include a tracking or location monitoring system, in communication with the information device, for identifying the location of the information device. The information device may be a personal digital assistant, tablet personal computer, or mobile telephone, and may be operable to receive information input by the user. According to yet another aspect of the invention, the information device is operable to transmit the information input by the user to the server, which may occur via a local area network.

According to another embodiment of the invention, there is disclosed a computer program product for identifying context relevant information. The computer program product includes a computer-readable storage medium having computer-readable program code portions stored therein, the computer-readable program code portions including a first executable portion for accessing context-relevant information associated with a user associated with a WID, and a second executable portion for identifying, based at least in part on the identity of the user, the location of the WID, and the proximity of the WID to at least one person or object, context relevant information for transmission to the WID. According to one aspect of the invention, the computer readable code portions are executed at a server local to a hospital. According to another aspect of the invention, the second executable portion may identify the context relevant information based on display rules, established at least in part by the user.

According to yet another embodiment of the invention, there is disclosed an apparatus for receiving information. The apparatus includes a wireless receiver operable to receive context relevant information, and at least one display (e.g., a touch sensitive screen) operable to present the context relevant information to a user, where the context relevant information is transmitted to the apparatus by at least one server in communication with the apparatus, and where the context-relevant information based at least in part on the identity of a user associated with the apparatus, the location of the apparatus, and the proximity of the apparatus to a person or object.

According to one aspect of the invention, the apparatus includes a wireless transmitter, where the wireless transmitter is operable to identify the location of the apparatus. According to another aspect of the invention, the apparatus also includes a user input operable to receive information that identifies the user and/or the location of the apparatus. The at least one display may also be operable to display a plurality of fields that display the context-relevant information. Furthermore, the size and location of the at least one field in which context relevant information is displayed may be configurable by the user.

According to another embodiment, there is disclosed a method for providing context relevant information. The method includes identifying a user associated with a WID, storing information rules established at least in part by the user, and receiving location information identifying the location of the WID. The method also includes determining the user's context based at least in part on the user's identity, the location information, and the proximity of the WID to an object or person, and transmitting to the WID context-relevant information that corresponding to the user's context, where the context-relevant information is defined at least in part by the information rules.

According to one aspect of the invention, the method also includes the step of receiving information input by the user into the WID. According to another aspect of the invention, the step of storing information rules further includes the step of storing display rules that establish how the context relevant information is automatically displayed on the wireless device. The step of determining the user's context may also be based at least in part on the identity of a person or object located near the WID. The identity of the person or object positioned nearby the WID may be determined by wireless communication. According to one aspect of the invention, the person may be a hospital patient.

According to another aspect of the invention, the user is identified based on a device associated with the user. The device may be a smart card, radio frequency tag, infrared tag, or barcode. The step of identifying the user may also include identifying the user based on biomedical indicia of the user. Furthermore, the step of determining the user's context may occur remote from the WID.

BRIEF DESCRIPTION OF THE DRAWINGS

Figure 1:
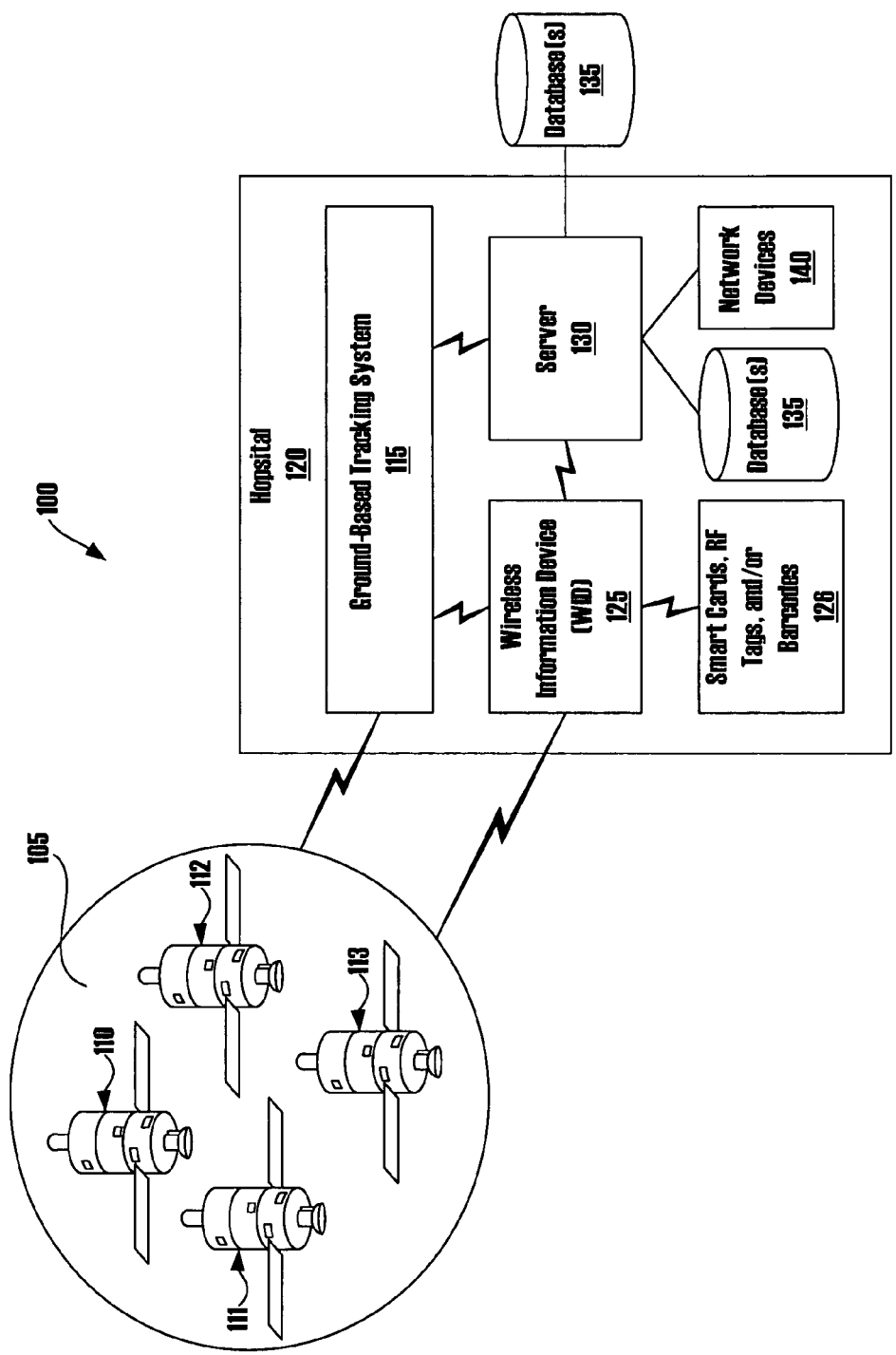

Having thus described the invention in general terms, reference will now be made to the accompanying drawings, which are not necessarily drawn to scale, and wherein:

FIG. 1 is a block diagram illustrating an exemplary system in accordance with certain exemplary embodiments of the present invention.

Figure 2:
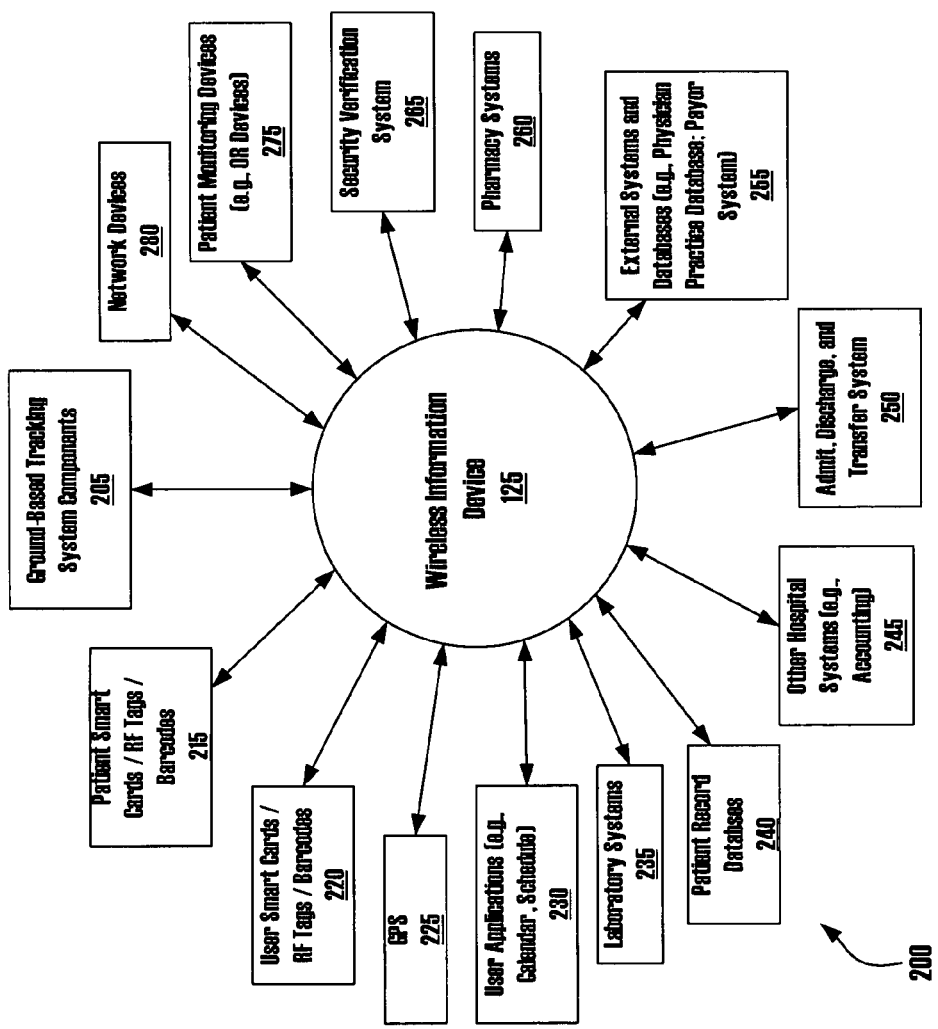

FIG. 2 is a block diagram illustrating the devices with which a WID is in communication, according to an illustrative example of one embodiment of the present invention.

Figure 3:
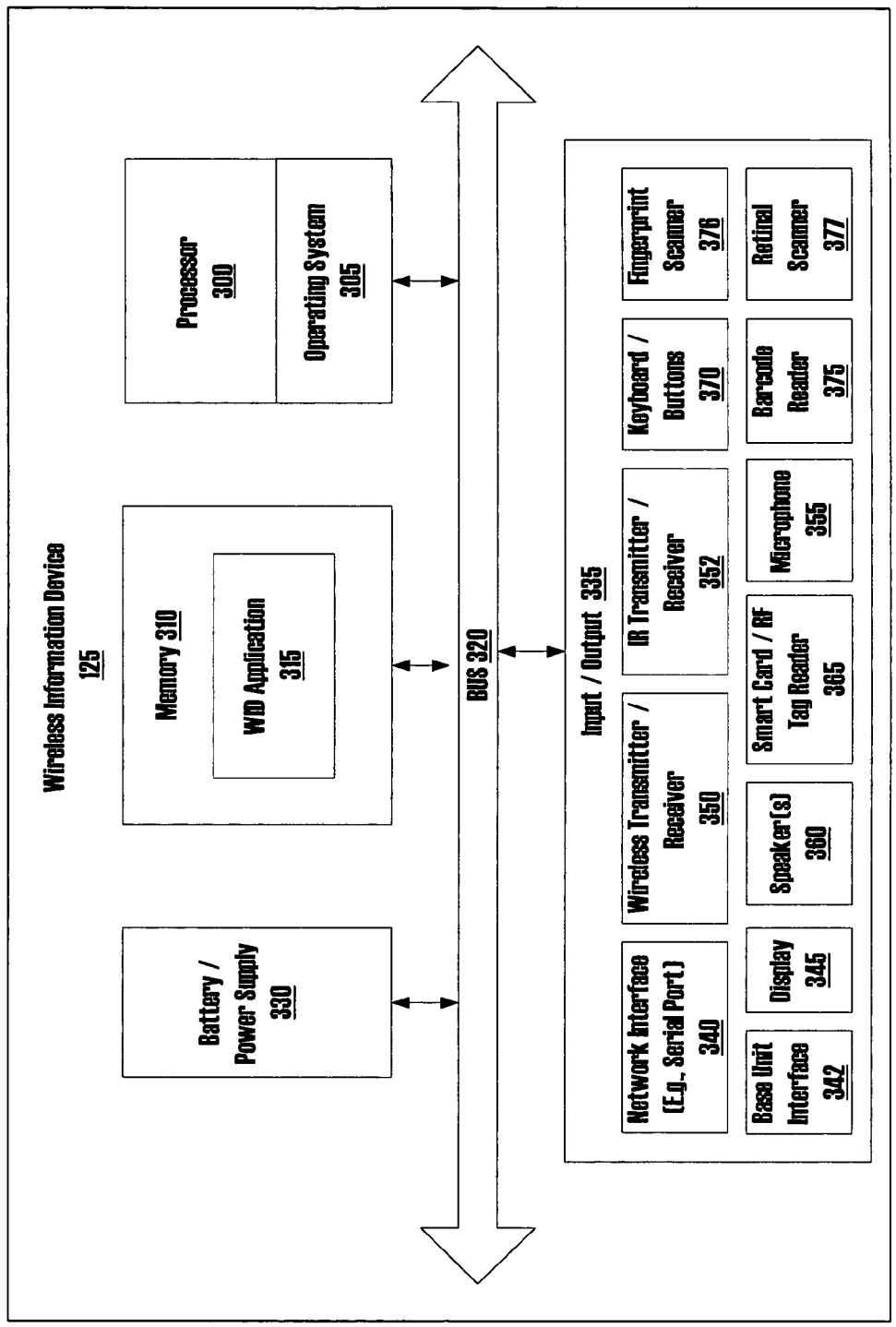

FIG. 3 is a block diagram showing the components of a WID, according to one embodiment of the present invention.

Figure 4:
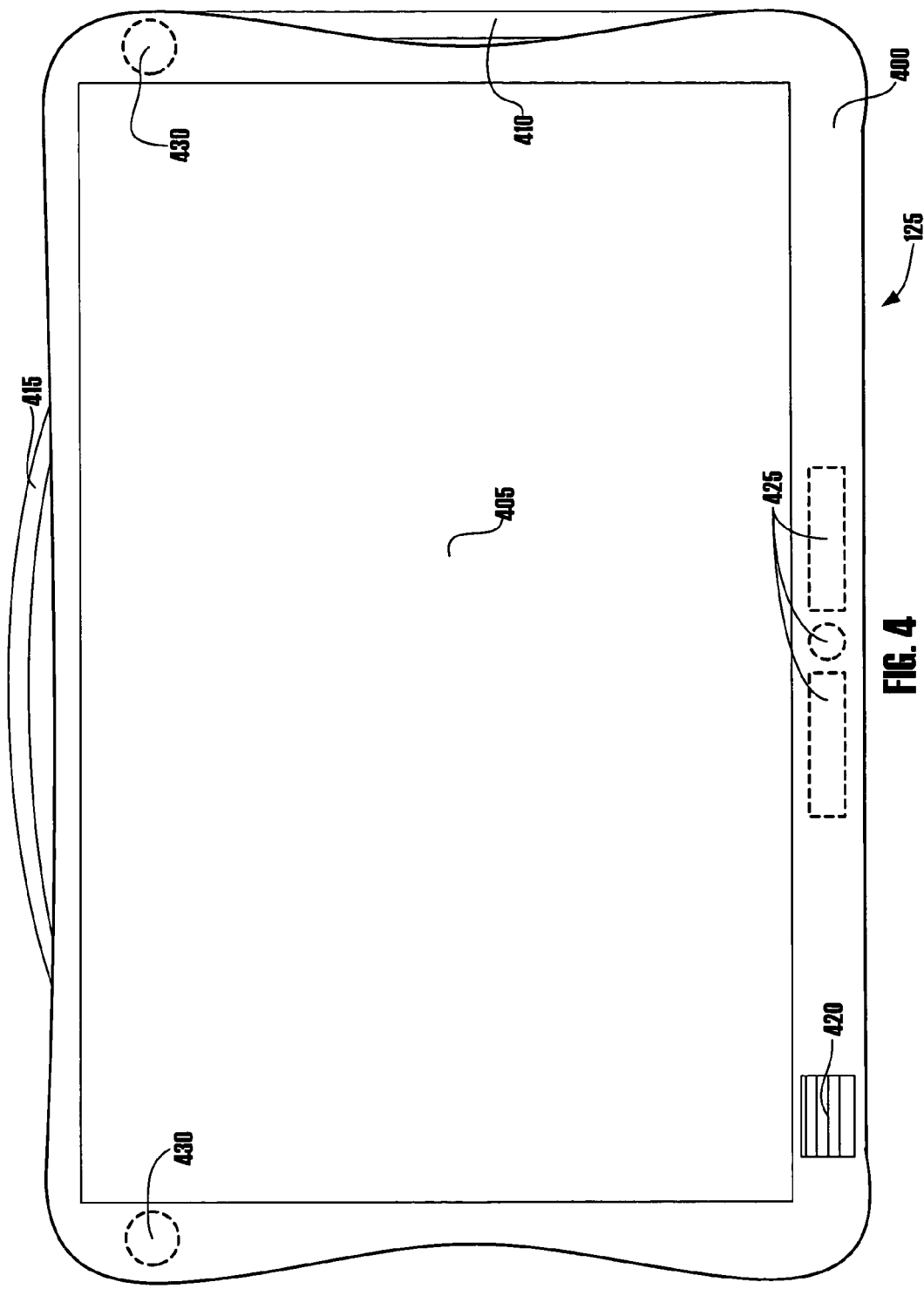

FIG. 4 shows an illustrative example of a WID, according to one aspect of the present invention.

Figure 5:
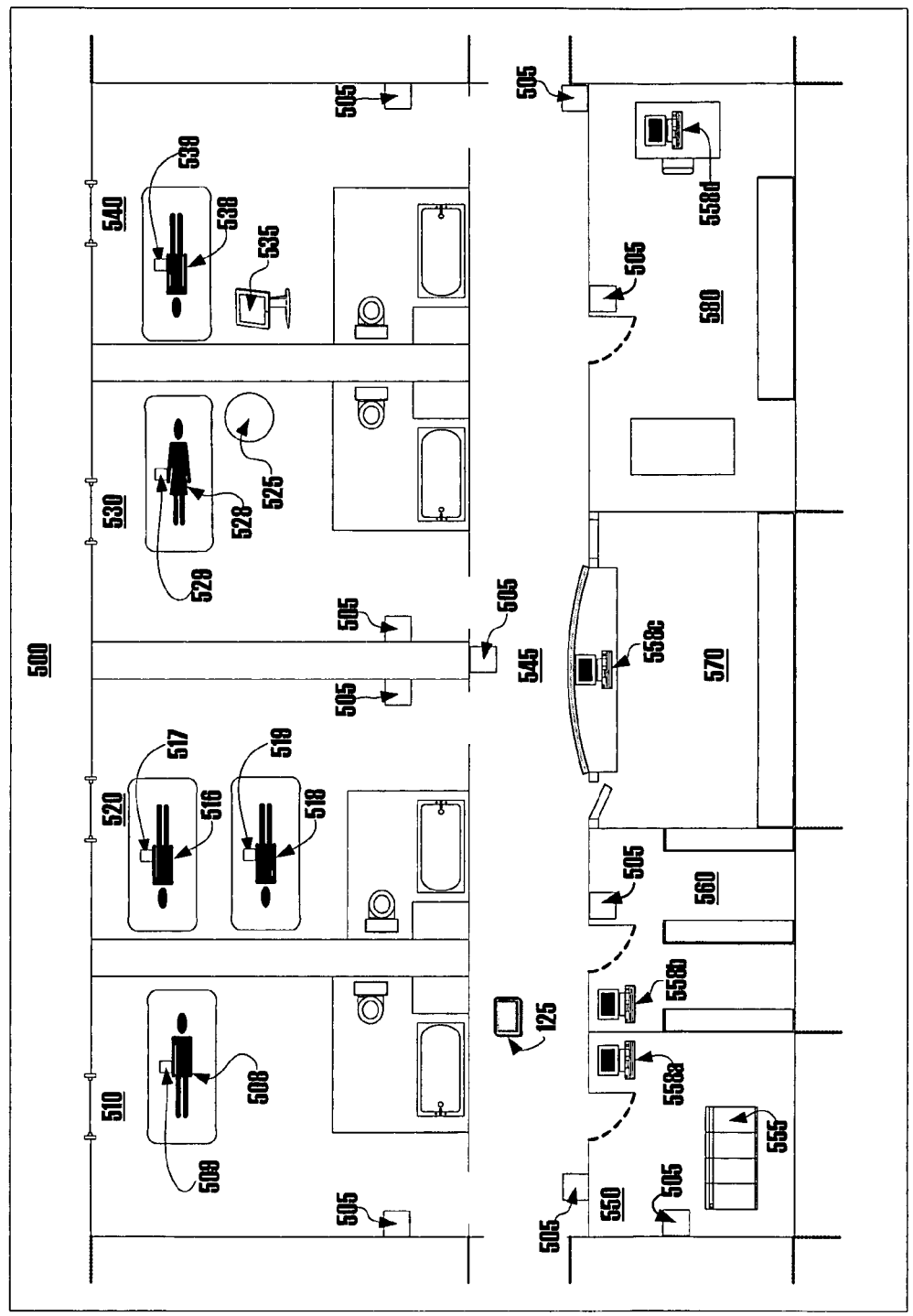

FIG. 5 is an illustrative hospital layout in which the system of the present invention operates, according to one embodiment of the present invention.

Figure 6:
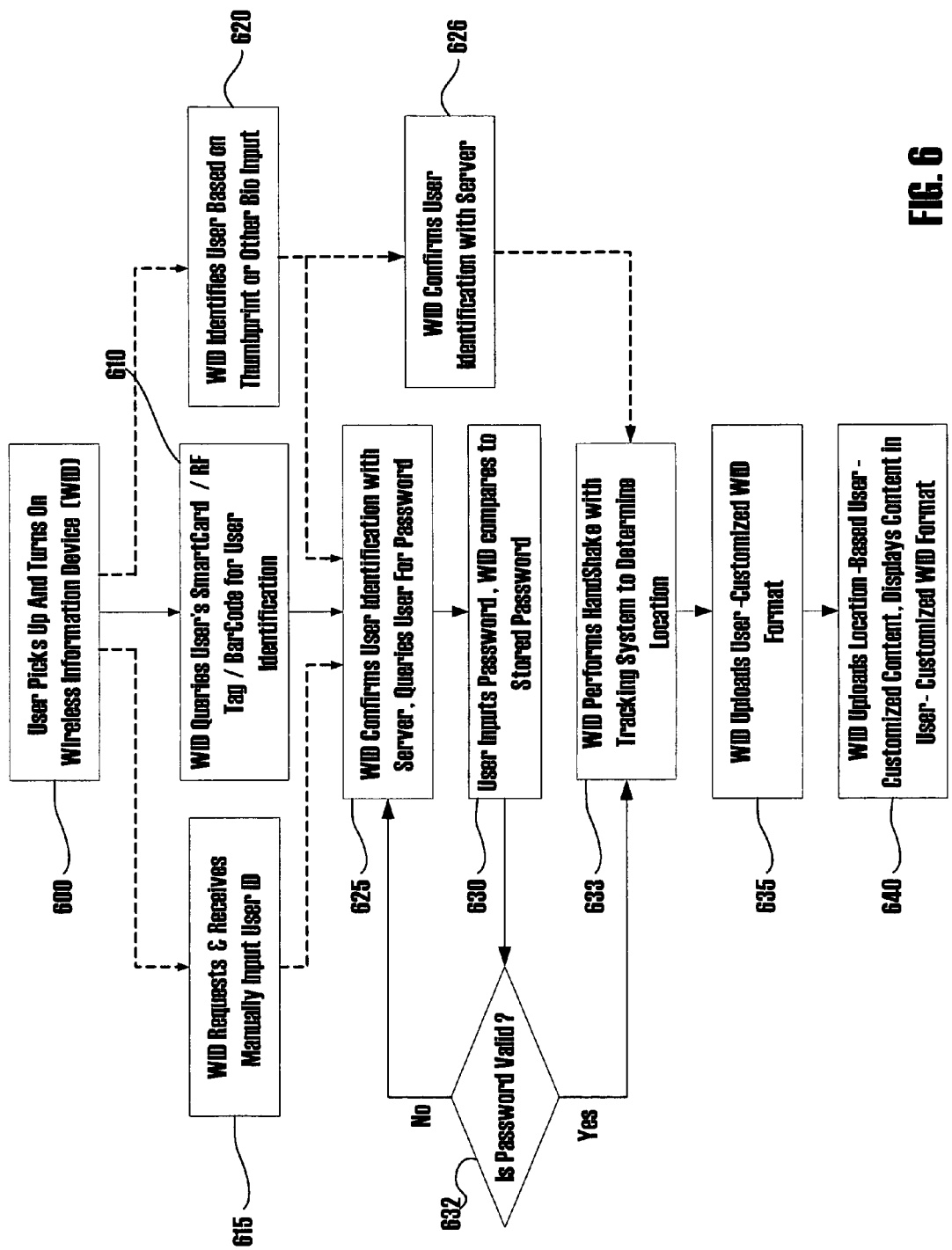

FIG. 6 is a block diagram flowchart showing a user log-in process to a WID, according to one embodiment of the present invention.

FIG. 7A shows the path of a user associated with a WID in the illustrative hospital layout of FIG. 5, according to an illustrative method and system of the present invention.

Figure 7B:
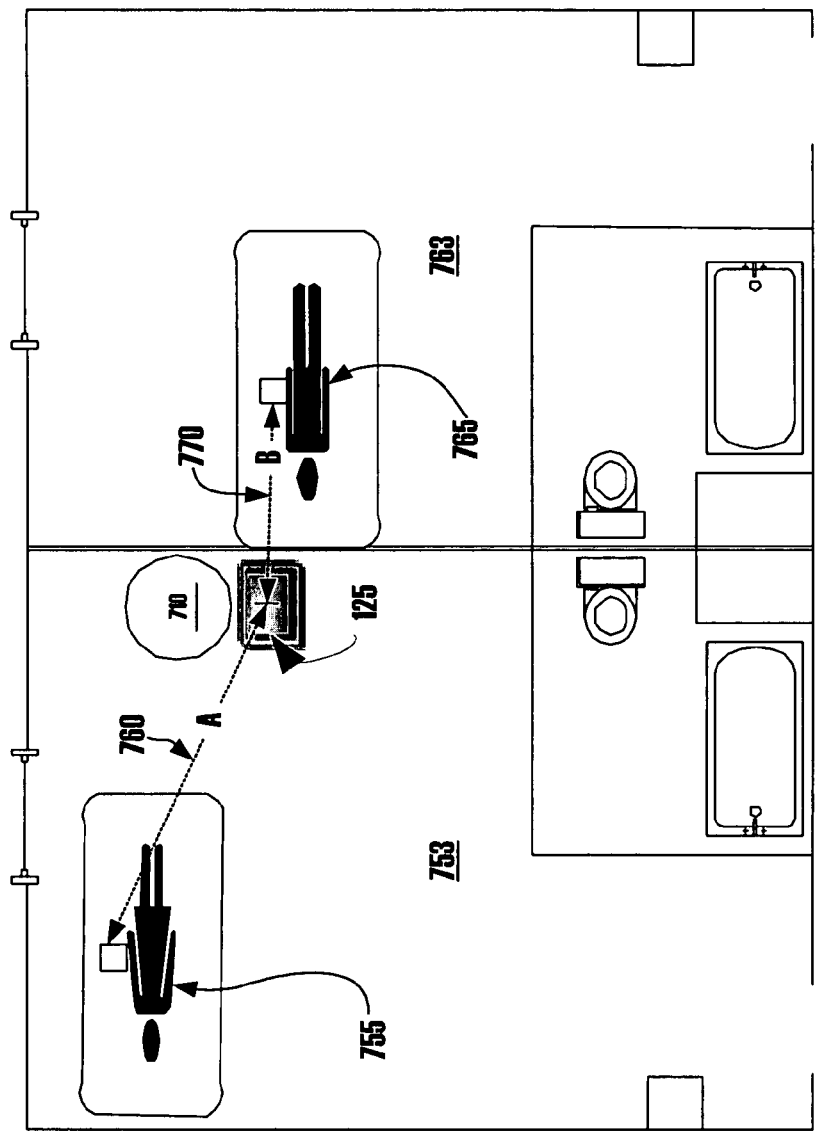

FIG. 7B shows a user associated with a WID located near two patients, according to an illustrative method and system of the present invention.

Figure 8:
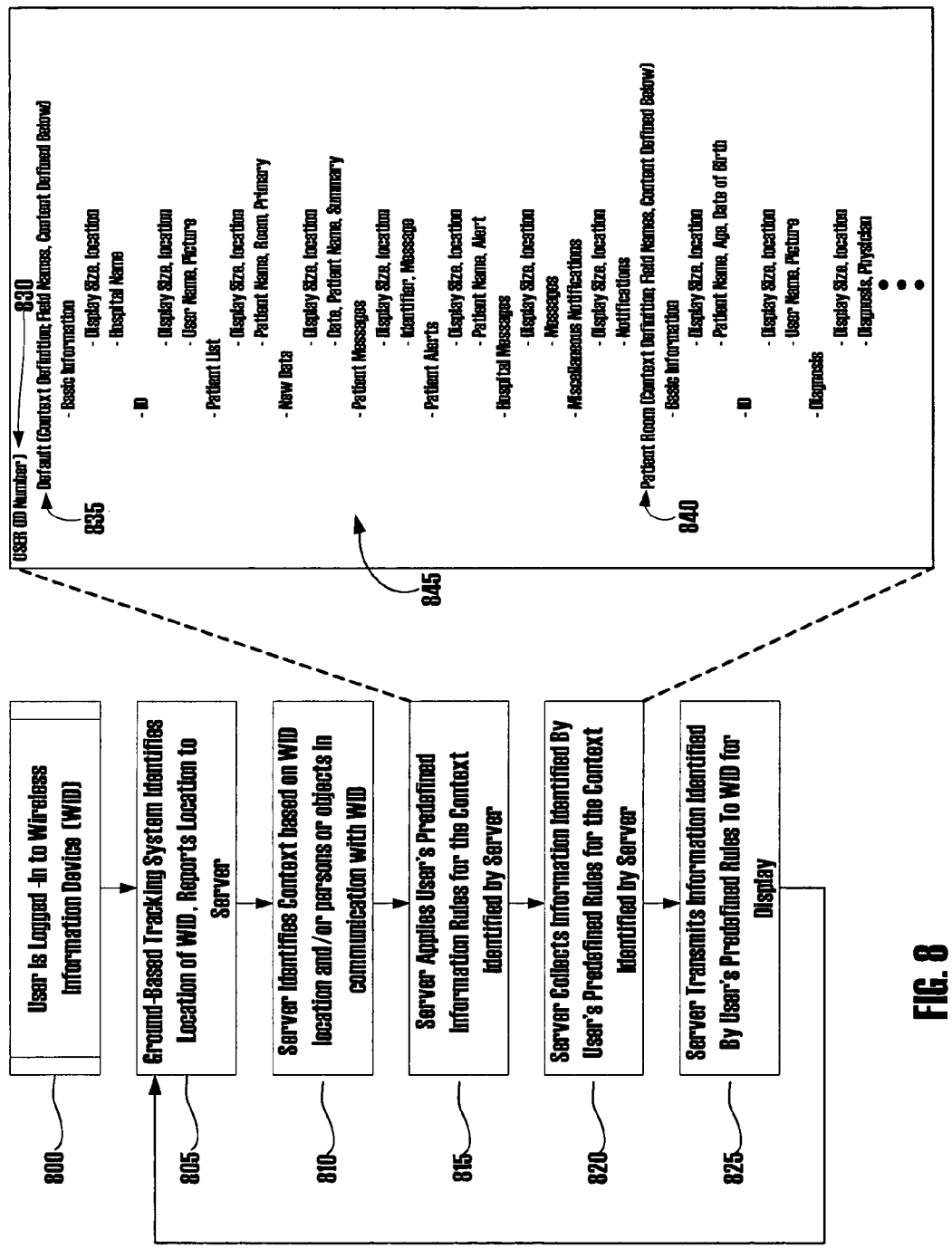

FIG. 8 shows a block diagram flow chart illustrating the serving of information to the WID based on a user's pre-defined display rules.

Figure 9:
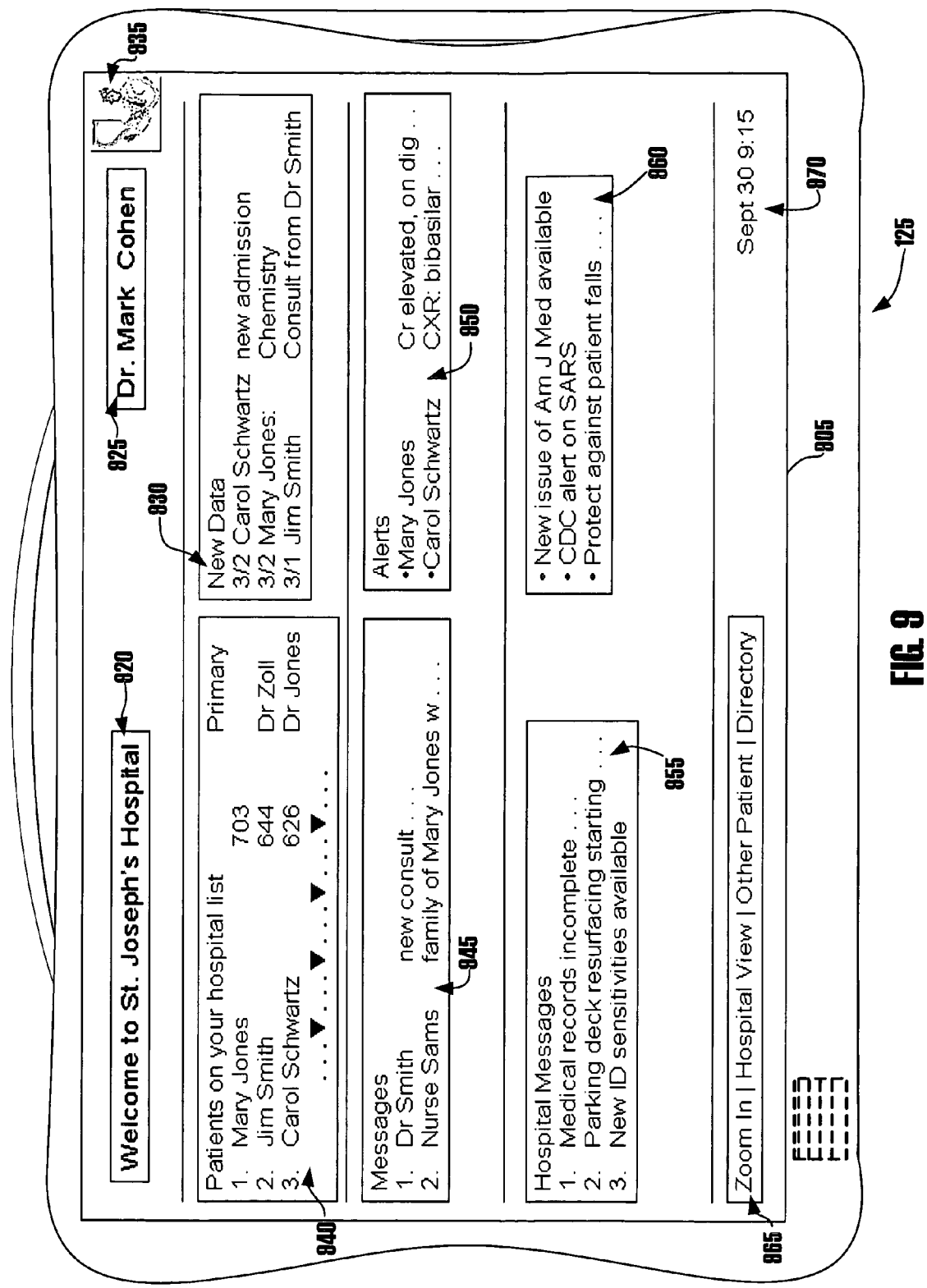

FIG. 9 shows an illustrative example of a WID display after a physician user enters a hospital, according to one illustrative example of the present invention.

Figure 10:
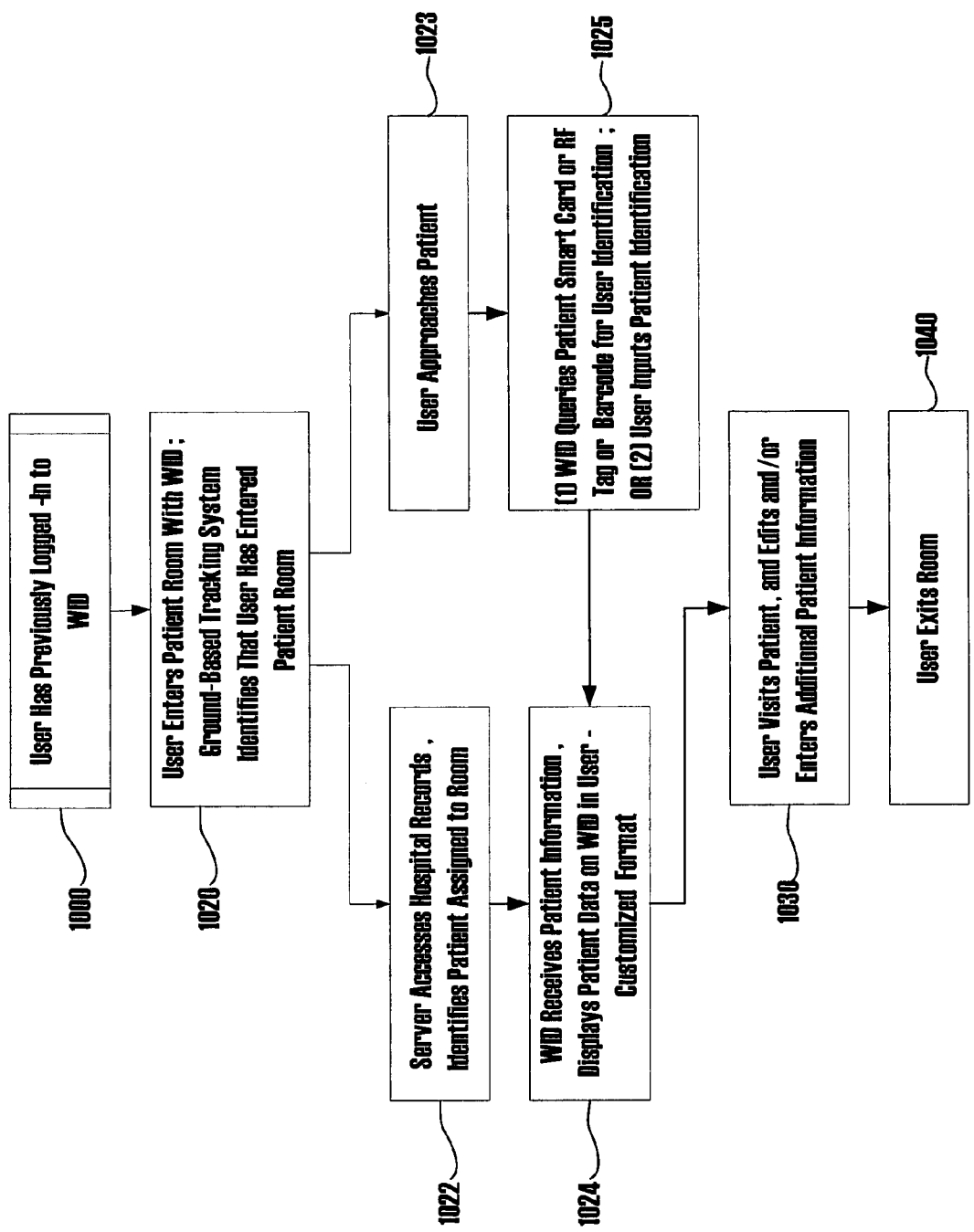

FIG. 10 is a block diagram flowchart showing the uploading of patient data to the WID, as a user moves via the path shown in FIG. 7A.

FIGS. 11-15 show illustrative examples of WID displays, according to multiple aspects of the present invention.

DETAILED DESCRIPTION OF THE PRESENT INVENTION

The present invention now will be described more fully hereinafter with reference to the accompanying drawings, in which preferred embodiments of the invention are shown. The present invention may be adapted for use in a wide variety of applications and is suitable for any environment in which personalized, context relevant information may be delivered to a person interacting with multiple and changing environments, persons and objects. By way of illustration and not by way of limitation, unless indicated otherwise, the preferred embodiment is presented in the context of a medical facility environment in which various healthcare workers (e.g. doctors, nurses, administrators, lab technicians, pharmacists etc.) require up-to-date and accurate context relevant information.

It will be appreciated to those of ordinary skill in the art that although the present invention is described in the context of a hospital setting, the present invention may be utilized in other environments, such as hotels, shopping malls, zoos, museums, and the like. Further, this invention may be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

I. System Hardware

FIG. 1 shows a context relevant information system 100 according to one embodiment of the present invention. The system 100 generally includes a Global Positioning System (GPS) 105 and a hospital 120 having a ground-based tracking system 115. The hospital 120 also includes at least one WID (WID) 125, a server 130 in secure, HIPAA compliant communication with one or more databases (internal or external to the hospital) 135 and network devices 140, and a plurality of smart cards, Radio Frequency (RF) tags, and/or barcodes 126. As illustrated in FIG. 1, the WID 125 is typically in wireless communication with the ground-based tracking system 115, server 130, and smartcards, RF transmitters, and/or barcodes 126. Although a hospital server 130 is described herein, it will be appreciated by those of skill in the art that the server 130 may be separate and in communication from a hospital server that acts as a hospital-wide computer server for effecting the functions of typical hospital computer systems. Therefore, the server 130 may be implemented as an add-on component that communicates with the one or more hospital servers and/or hospital equipment. Furthermore, although illustrated as internal to the hospital 120, the server 130 may be external to the hospital 120 and may be a dedicated to effecting the functioning of the system described herein.

Briefly, the GPS 105 and ground-based tracking system 115 work in tandem to precisely identify the location of the WID 125 inside the hospital 120. The WID 125 is an information display and data entry device carried by individual healthcare workers, such as physicians, nurses, lab technicians, and the like. The WID 125 may be a personal digital assistant (PDA), a tablet computer, a wireless phone, a handheld computer, a laptop computer, or like portable device. The WID 125 wirelessly receives information from and transmits information to the hospital server 130 and to the databases 135 and network devices 140 in wireless or fixed path communication with the server 130.

Based on its location within the hospital 120 the WID 125 automatically provides location-specific information to each user. Furthermore, the location-specific information is customized based on the identity of the user, such that each user will receive the location-specific information in a format and presentation useful to the user, as explained in detail below. Because the information provided by the WID may also be based on the proximity of the WID to persons and objects in addition to providing information based on user location and identity, the information is context-relevant information. The smart cards, Radio Frequency (RF) tags, and/or barcodes 126 are used to identify persons, such as the users carrying the WID 125, patients, and equipment. The WID 125 may wirelessly communicate with these devices, the ground-based tracking system 115 and the server 130 to provide the appropriate location-specific information.

As an illustrative example, when the WID 125 is picked up by a physician user, the WID 125 may identify the physician by a smart card carried by the physician, along with a password input by the physician. As the physician approaches a patient, the WID 125 may identify the patient by querying a smart card carried by the patient. The WID 125 may then communicate with hospital systems to retrieve patient information for display on the WID 125, which is provided in a customized format preferred by the physician. As another illustrative example, after a healthcare worker is identified by the WID 125, the WID 125 may provide the healthcare worker facility information as the worker moves throughout the hospital. Therefore, upon approaching a patient's room, the location of the WID 125 is identified, as is the identity of the room nearby the WID 125, and the patient's name may automatically be displayed on the screen. Because each user in the above examples may have varying degrees of access rights to view patient information, the WID 125 user's identification is used to customize the information received by the WID 125, as well as the format in which the WID 125 presents the information. These and other illustrative examples are described in further detail below.

A. GPS and Ground-Based Tracking System

Referring again to the system 100 shown in FIG. 1, the GPS 105 includes a plurality of GPS satellites 110, 111, 112, 113, which transmit signals that can be used by the ground-based tracking system 115 and WID 125 for navigation. Typically, in order to effectively operate a navigation system using the GPS satellite signals, at least four satellites must be in view at all times. Unfortunately GPS satellite signals are relatively weak microwave signals that cannot penetrate through obstacles such as hospital walls. Because there is no direct line-of-sight reception of the satellite signals within the hospital 120, the precise location of the WID 125 cannot be tracked using the GPS 105 alone. Therefore, the ground-based tracking system 115 is employed to work in conjunction with the GPS 105 to provide position signals to the WID 125, which includes a GPS receiver. It should be appreciated that although the ground-based tracking system 115 is illustrated as being contained within the hospital, the ground-based tracking system 115 may include at least one GPS receiver located outside of the hospital, such as on the roof of the hospital. This permits the ground-based tracking system 115 to receive GPS satellite signals without suffering from line-of-sight problems.

The use of a ground-based tracking system 115 permits the location of the WID 125 to be tracked with great accuracy within the interior of the hospital 120. According to one aspect of the present invention, a GPS and ground-based tracking system used to effect tracking of one or more WIDs of the present invention is disclosed in U.S. Pat. No. 6,459,989, titled "Portable Integrated Indoor And Outdoor Positioning System And Method," the entire contents of which are incorporated herein by reference as if set forth fully herein. Thus, according to one embodiment of the present invention, to effect accurate positioning information a base station GPS receiver may be located outside of the hospital 120 at a fixed position and may be in communication, using an indoor antenna or the like, with one or more indoor communication units placed throughout the interior of the hospital 120 that provide pseudo-GPS signals. The WID 125, using a GPS receiver and differential GPS corrections, as are well known in the art, may then accurately establish its location at any position in the hospital 125 to within a foot or less. As shown in FIG. 1, the WID 125 may also be in direct wireless communication with the GPS 105 when line of sight problems do not exist, which may occur in other environments in which the present invention may be used.

Although the present invention is illustrated in FIG. 1 and described herein with reference to a GPS 105, it will be appreciated that the ground-based tracking system 115 can also effect accurate tracking of the WID 125 in the interior of the hospital 120 without the use of the GPS 105. For instance, the ground-based tracking system 115 may rely entirely on a large number of indoor communication units that receive RF or other signals transmitted by the WID 125 as it moves through the hospital, which are in turn used to accurately identify the position of the WID 125. For example, the rough position of the WID 125 may be obtained by determining which local antennas receive communications from the WID 125, and more precise location information may be obtained using time-of-flight and triangulation techniques, as are known in the art.

According to another embodiment of the present invention, the WID 125 may form a local RF Bluetooth link with communications equipment throughout the hospital 120 to identify the location of the WID 125. As will be appreciated by those of ordinary skill in the art, Bluetooth requires that low-cost transceiver chips be included in each device, where the transceiver transmits and receives in a frequency band of 2.45 GHz. Some advantages of using Bluetooth in the hospital 120 are that each device would have a unique 48-bit address from the IEEE 802 standard, data could be exchanged at a rate of 1-2 megabits per second, devices could be configured to communicate in areas with high electromagnetic interference, and transmissions would have built-in encryption and verification.

Regardless of which of the above systems and methods are used for indoor tracking, the ground-based tracking system 115 is operable to accurately track the location of the WID 125 as it moves throughout the hospital 120. Because the location of the WID 125 is known, information corresponding to fixed objects may be displayed on the WID 125 as the WID 125 moves throughout the hospital 120. For instance, as a healthcare worker moves past a particular room, the room may be identified on the WID 125, along with information associated with the room (e.g., patient information) and retrieved via the hospital server 130, such as the room occupant or other information associated with the room and stored in database(s) 135.

Although the WID 125 can utilize the ground-based tracking system 115 to effectively identify objects based on their fixed position, according to one embodiment of the present invention the WID 125 is further operable to identify mobile objects and persons using smart cards, RF tags and/or barcodes 126 associated with each mobile person or object. For instance, the WID 125 can be used to identify that it is positioned close to a patient carrying a smart card, regardless of the patient's location or position in the hospital 120.

B. Smart Cards, RF Tags and Barcodes

Moving persons and objects within the hospital 120 preferably each carry a smart card, RF Tag, or barcode 126 for identification purposes. For instance, healthcare workers, patients and objects carry smart cards, RF Tags and/or barcodes 126 to identify themselves to the WID 125. Therefore, as is explained in detail with respect to FIG. 3, below, the WID 125 includes a smart card, RF Tag, and/or barcode reader to identify each object associated with the smart card, RF Tag, and/or barcode 126.

Smart cards, as are known in the art, are relatively inexpensive and can include an embedded microchip that can be loaded with data for use in identity establishment. When the smart cards are less than approximately a foot from a smart card reader within the WID 125 the information on the smart cards, typically a user ID, can be wirelessly read or accessed by the WID 125. RF tags, which are also known in the art, perform similar functions to smart cards, though they can have greater read ranges than smart cards. Passive RF Tags, which are similar to smart cards, or active RF Tags, may be used. Active RF Tags are powered, and therefore are heavier than passive tags, more expensive, and offer limited operational life in comparison to passive tags. However, active RF Tags may be advantageous because they require a lower-power reader than passive tags and permit long read ranges, up to hundreds of feet.

Both smart cards and RF Tags come in a variety of different shapes and sizes and can be placed in many different types of casing such as plastic cards, stickers, wristbands, labels, and the like. According to a preferred embodiment of the present invention, RF Tags are carried by healthcare workers in card form, such as incorporated with an employee ID card, and patients carry RF Tags in patient wristbands. Barcodes, as are known to those of skill in the art, can also be placed on wristbands or on stickers and may alternatively be used to identify persons and objects in the hospital 120. However, barcodes are less preferred than smart cards or RF Tags because the WID 125 would require a barcode reader to read the sequence of vertical bars and spaces comprising the barcode, rather than merely be in its presence, as with smart cards and RF Tags. Nevertheless, barcodes are advantageous to identify hospital patients because they are extremely inexpensive as compared to smart cards and RF tags. Other identification means may also be used, such as infrared tags. Alternatively, manually-input personal ID codes may be used to identify each person in the vicinity of the WID 125, though such a system is less preferred because it is not automated and creates the opportunity for input error.

According to another embodiment of the present invention, the system 100 may operate without devices that communicate directly with the WID 125. For instance, every moving object in the hospital 120 may be associated with an active RF tag, GPS receiver/transmitter or like position transmitter, or similar device, that communicates directly with the ground-based tracking system 115, such that the location of everything in the hospital 120 is tracked by the ground-based tracking system 115. In this embodiment the WID 125 does not communicate directly with patient devices, but relies on the ground-based tracking system 115 to notify the WID 125 when it is in the vicinity of another person or object. Therefore, the ground-based tracking system 115 may contain logic identifying when a WID 125 is in the vicinity of a particular patient having an RF tag, GPS transmitter, or like device, associated therewith. According to one aspect of the invention, using this embodiment the ground-based tracking system 115 can track all users' location in the hospital 120. The ground-based tracking system 115 facilitates the serving of appropriate content to the WID 125 by establishing the identification of the user associated with the WID 125. This alternative embodiment may be advantageous because it allows all items in the hospital 120 to be tracked, and does not require the active identification of objects and persons by the WID 125. Nevertheless, such a system is more expensive and relies on more sophisticated hardware than a preferred system in which the WID 125 queries smart cards, RF tags and/or barcodes 126 to ascertain the identification of a moving person or object.

As previously explained, by knowing its location, the user-ID and patient ID (e.g., queried from a smart card, RF tag or barcode) the WID 125 can present location-specific information to users where the information presented, and the format in which it is displayed, is configurable on a user-by user-basis. Consider the illustrative example of a patient visited in his or her room prior to surgery by two doctors, including the patient's anesthesiologist and surgeon, where both carry a respective WID 125. Although the patient's identity and location remains the same, the information displayed to the anesthesiologist may differ from the information displayed to the surgeon. This occurs because the WID 125 initially identifies the user associated with it (i.e., the anesthesiologist or surgeon), and presents patient information to that individual based on that user's predefined display rules, as will be described in greater detail below with respect to FIG. 8. Continuing with the same illustrative example, even if the patient had two surgeons visit the patient, each with the same specialty, each surgeon may view their own personalized version of the data associated with the patient. Nevertheless, in the above examples all of the patient data is accessible by the physicians via the WID 125.

C. WID Access to Databases and Network Devices

Referring once again to FIG. 1, the WID 125 may be in communication with database(s) 135 and network devices 140 via the hospital server 130. Preferably, the WID 125 is a thin-client, where the information displayed on the WID 125 is stored on the one or more database(s) 135 and served to the WID 125 by the server 130. Therefore, it is preferred that the WID 125 only contain memory to temporarily store data prior to its transmission to the server 130, either wirelessly or via a docking station for the WID 125. The central storage of information in the system 100 is advantageous because a plurality of WIDs may be used by healthcare workers, and each WID 125 does not have to be associated with a particular patient or healthcare worker. For instance, the hospital 120 may contain a large number of WIDs 125, where any WID 125 can be picked up by any healthcare worker. Because the location of each WID 125 is known, as is the identity of the user carrying the WID 125, each WID 125 can serve context relevant information to each user according to user-defined display rules. According to one embodiment of the present invention, prior to being picked up by a healthcare worker, the individual WIDs 125 do not contain any user, hospital or patient information, as all of the information displayed on the WID 125 is received wirelessly from the server 130. As explained in greater detail with respect to FIG. 3, the WID 125 may only contain sufficient memory to temporarily store wirelessly received information prior to its display on the WID 125, and to run a thin client application that facilitates display and entry of information.

Information for display on the WID 125 may be retrieved by the server 130 from internal hospital 120 database(s) 135. For instance, the database(s) may include data including patient records, lab results, pharmacy data, admit, transfer or discharge information, accounting information, X-Rays, MRIs. CT and/or PET scans, practice guidelines, or any other type of information that may be useful to a hospital healthcare worker to process or treat a patient. The information may also be retrieved by the server 130 from database(s) 135 external to the hospital, such as payer databases (e.g., insurance providers), drug information databases, or databases maintained by healthcare workers external to the hospital 120, such as physician databases containing patient information, physician schedules, or any other physician practice information. Therefore, the WID 125 has access to all data that may be useful to aid a healthcare worker in treating or processing a patient, as well as data that may be useful to the healthcare worker in his or her administrative or other capacities.

In addition to information retrieved from database(s) 135, the server 130 is further operable to serve the WID 125 with data obtained from network devices 140 in communication with the server 130. These devices can include hospital hardware, such as patient monitors, and the like, which are either in wireless or hardwired communication with the server 130. As a result, a healthcare worker can quickly view on the WID 125 any important information measured by hospital hardware.

FIG. 2 illustrates some of the systems and components in communication with the WID, either directly or via the server 130. These include: ground-based tracking system components 205; patient or user smart cards, RF tags, or barcodes 215, 220; the GPS 225; user applications stored on hospital systems (e.g., calendars, schedules and the like) 230; laboratory systems 235; patient record databases 240; pharmacy systems 260; admit, discharge and transfer systems 250; security verification system 265; other hospital systems (e.g., accounting, inventory, etc.) 245; external systems and databases (e.g., physician practice systems or databases, or payer systems or databases) 255; patient monitoring devices 275; and network devices (e.g., other hospital devices that are not patient monitoring devices) 280. Additional systems and components that may communicate with the WID 125 but are not illustrated include systems and components that permit a user to view, access and/or input email, practice guidelines, images (including X-Rays, MRIs, CT-PET scans, photos, etc.) and other medical information. Those of ordinary skill in the art will appreciate that additional systems and components may be in communication with the WID 125, though not illustrated in FIG. 2 or disclosed herein.

Information is preferably transmitted to the WID 125 in a common format and protocol to minimize the processing required by the WID 125. Therefore, information served to the WID 125 from the server 130 may undergo a translation into an appropriate format, as is well known to those of skill in the art, prior to its transmission to the WID 125. According to one aspect of the present invention, the WID 125 displays HTML or XML data, where the WID need not filter any information transmitted to it because the server 130 only transmits information that meets the user's predefined display rules for a particular context. This process is explained in greater detail with respect to FIG. 8, below. According to another embodiment of the present invention, the WID 125 may also contain software for translating information received in different formats and protocols. Next, an illustrative embodiment of a WID 125 is considered with reference to FIG. 3.

II. The WID

An illustrative embodiment of a WID 125 is shown in block diagram form in FIG. 3. To begin, it should be noted that the present invention is described below with reference to block diagrams and flowchart illustrations of methods, apparatuses (i.e., systems) and computer program products according to an embodiment of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Referring once again to FIG. 3, there is shown in block diagram form a WID 125. The WID 125 is a light weight mobile display and data entry device that may be embodied as a personal digital assistant (PDA), a tablet computer, a wireless phone, a handheld computer, a laptop computer, or similar device. As illustrated in FIG. 3, the WID 125 includes a processor 300, memory 310, battery or power supply 330, input/output components 335, and a bus 320 to effect communication in between each of the above.

The processor 300 controls the operation of the WID 125 with the aid of the operating system 305. The operating system 305 may be any well-known operating system, such as Windows CE™ or Microsoft XP Tablet PC Edition™, which executes the instructions of the software applications residing within the memory 310. It will be appreciated by those of ordinary skill in the art that the operating system 305 also perform basic tasks such as recognizing inputs, sending outputs to display devices, and controlling disk drives and peripheral devices.

The WID application 315 within the memory 315 is operable to effect the functions of displaying information as described in detail herein. The WID application 315 also effects the functions of receiving user inputs, and for transmitting the user input data to the hospital server 130. Furthermore, the WID application 315 enables the WID 125 to receive communications from the server 130, ground-based tracking system 115 and smart cards, RF Tags, and/or barcodes 126 to identify the location of the WID 125 and to receive data for display on the WID 125.

It is preferred that the battery/power supply 330 of the WID 125 be sufficient to maintain continuous service for a minimum of six to twelve hours, and be largely recharged within a short time frame. In any event, the WID 125 may also include a removable and rechargeable battery pack (not illustrated) which is removable for charging batteries at a base unit, as described in greater detail below.

As shown in FIG. 3, the WID 125 includes multiple input and output components 335 for receiving and transmitting information. These may include: network interface 340, base unit interface 342, wireless transmitter/receiver 350, an IR transmitter/receiver 352, a keyboard and/or buttons 370, display 345, speaker(s) 360, microphone 355, smart card and/or RF tag reader 365, and barcode reader 375. Each of these input/output components 335 are considered in detail next.

A. WID Input/Output

The network interface 340 may a serial port, parallel port, USB port, or the like, by which the WID 125 can communicate via hardwires with the hospital server 130. Although it is preferred that the WID 125 communicate wirelessly with users, objects and other computers, including the server 130, the WID 125 of the present invention may also be used as a stationary display and data entry device that is hardwired to the server 130. This may be advantageous in environments such as an Operating Room (OR), where the WID 125 could be a fixed display rather than carried into and out of the OR. Furthermore, using the WID 125 as a fixed display would permit it to be much larger. For instance, the WID could be a plasma television or large flat screen monitor. Despite it being capable of being a fixed display, the WID 125 would perform the same functions when fixed as it would if mobile—the serving of context-based and customized information. The network interface 340 therefore permits the WID 125 to receive and transmit the same information via hardwires that it may otherwise receive and transmit wirelessly. Moreover, it will be appreciated that the network interface 340 may also be used for diagnostics on wireless WIDs 125, and to update the WID application 315 as needed.

The base unit interface 342 may include one or more elements that engage a base station to permit the WID 125, and more specifically the battery/power supply 330, to be charged and recharged. According to one embodiment of the present invention, the WID 125 preferably resides, when not in use, in a base unit at a nursing station or other centrally located area, or in a wall mounted base unit in a patient room. The base includes suitable recharging circuitry which serves to recharge the battery/power supply 330 via the base unit interface 342 when the WID 125 is at rest in the base unit. The base unit, in turn, includes an electrical plug arrangement for interconnection with an AC outlet or other suitable power supply. The base unit may also includes a suitable locking mechanism which locks the WID 125 in the base unit such that the WID 125 is only released for use by authorized users.

When the WID 125 is used with a wall-mounted base unit in the patient room the base station may also be connected to the hospital server 130 to display hospital-related information to patients via the display 345. For instance, nurse names, lunch menus, or other information pertaining to the patient or patient's room may be displayed when the WID 125 is in the base unit. It will also be appreciated that the base unit interface 342 may be combined or integrated with the network interface 340, such that a WID 125 is connected to a hospital network when resting in the base station.

The display 345 of the WID 125 is preferably a liquid crystal, back lighted touch screen display, though it may also be an LCD display, CRT display, plasma display, LED display, or any other display known in the art capable of displaying text and graphical information. Additionally, as will be explained in greater detail below, it is preferable that the display 345 be capable of displaying textual information in multiple colors. According to one embodiment of the present invention, the display 345 is a touch screen display that presents a graphical keyboard to a user for input using fingers, a stylus, or pen, such that a keyboard 370 is obsolete. Preferably the WID 125 facilitates data input via the touch screen display 345 while the WID 125 is resting in the hand or on a flat surface to permit one-handed operation of the WID 125 at the point of care. Additionally, graphics displayed on the display 345 may be used to facilitate data entry; for example, injection sites may be selected from a graphical representation of the body, and temperature may be selected from a graphical representation of a thermometer. The display 345 also preferably includes status lights for indicating miscellaneous status of the WID 125 such as the battery life remaining in the WID 125.

The smart card and/or RF tag reader 365 is operable to communicate at a distance of a few inches or more from smart cards and/or RF tags carried by the WID 125 user, patients or objects. A bar code reader (or scanner) 375 may also be incorporated into the WID 125 to wirelessly identify items with bar codes such as patients and objects. This may also allow the WID 125 to identify items in environments other than in hospitals, such as in stores, restaurants, and the like. According to one aspect of the present invention, the WID 125 may identify pills based on barcodes associated with the pills. The WID 125 may accompany a nurse distributing pills to patients, where the WID 125 confirms that the medication and dose provided to a particular patient is correct.

The wireless transmitter/receiver 350, such as an RF modem or RF transceiver, is used for wireless transmission of information to the ground-based tracking system 115. Preferably, the wireless transmitter/receiver 350 is operable to effect all wireless communications with the ground-based tracking system and server 130. Therefore, the wireless transmitter/receiver 350 preferably effects all wireless communication of the WID 125, but for communication with smart cards, RF tags, and barcodes 126, which is performed by other input/output components 335 described above. The WID 125 may also contain an IR transmitter/receiver 352 for communicating with any additional objects that communicate via IR, such as patient monitoring devices. Though not illustrated in FIG. 3, it is contemplated that additional transceivers may also be incorporated into the WID to communicate with other electrical devices requiring alternative communication means.

As noted above, the WID 125 can include a keyboard and/or buttons 370 to assist a user with inputting data into the WID 125. The keyboard and/or buttons (hereafter collectively "keyboard") 370 may be integrated into the WID 125 or may be attached to the WID 370 as a peripheral device. The keyboard 370 may include dedicated function keys so as to allow an increase in customized specific instructions or notes to be input to the WID 125. The keyboard 370 may also include a built-in mouse or mouse pad, along with selection buttons and/or scroll devices as would be found on a conventional computer mouse.

A microphone 355 is preferably incorporated into the WID 125 to receive audio such that the WID 125 can act as a dictation device. According to one embodiment of the present invention, voice recognition is performed on words spoken by the user to input data into the WID 125. According to an alternative embodiment, the voice inputs are transmitted, without performing voice recognition, directly to the server 130 such that the WID 125, and more specifically, the WID application 315, need not include a voice recognition capability. The latter is preferred because voice inputs received via the microphone 355 can be translated into digital form and then transmitted to the server 130, to avoid the WID having to recognize a particular user's voice patterns.

Voice inputs received via the microphone 355 are preferably compressed and then converted into digital signals for temporary storage in the WID memory 310 prior to their transmission to the server 130. Alternatively, the voice inputs may be stored digitally in one or more databases that may exist within the WID 125, though not illustrated in FIG. 3. Although the WID 125 can immediately transmit the digitized voice inputs to the server 130 in real-time or near real-time, the storing of voice inputs will reduce the amount of wireless transmissions in the hospital environment. Furthermore, where a large amount of dictation is received by the WID 125, the WID 125 may be capable of requesting that the WID 125 be docked in a base unit or hooked up to the hospital network via the network interface 340 to transfer a large amount of digital voice data. Upon receiving the digital voice input the server 130 may carry out voice recognition by implementing a voice recognition algorithm in conjunction with templates previously made from a user's voice and stored. These algorithms may be local or remote from the WID 125. According to one aspect of the invention, the WID application 315 may perform these functions.

Speaker(s) 360 may be used to playback dictation, page the healthcare worker, or play other audio content that may be received by the WID 125, such as audio associated with video content. Furthermore, other input/output 335 components include a fingerprint scanner 376 and a retinal scanner 377, which as described in greater detail below, may be operable to perform fingerprint and retinal scans, respectively, to identify the user-holder of the WID 125.

Other input/output devices not illustrated in FIG. 3 may also be incorporated into the WID 125. For instance, according to one aspect of the present invention, the WID 125 may include a digital camera. This would permit a physician, nurse, or other user to take photographs that may be later accessed by a user via the WID 125. This may permit a photographic record of a medical condition, patient state, or the like. According to another aspect of the invention, the digital camera could be a digital video camera that records digital video, such as MPEG-2 or MPEG-4 video. This may be advantageous where the user wishes to capture a condition best represented by video rather than a written description and/or photographs. Other input/output features may also be included in the WID 125, as will be appreciated by one of ordinary skill in the art.

B. WID According to One Illustrative Embodiment

An illustrative WID 125 according to one aspect of the present invention is shown in FIG. 4. The WID 125 includes a plastic case 400 housing a touch sensitive, back-lit LCD screen 405. The screen 405 is capable of displaying text and graphics in black-and-white or color. The WID 125 illustrated in FIG. 4 also includes an optional handle 415 attached to the case to facilitate carrying of the WID 125. The WID 125 also includes a pen or stylus 410, which may be removably engaged into clips or nodes on the case 400. As is also illustrated in FIG. 4, the WID 125 can also include at least one integrated microphone 420, and integrated speakers 430. Furthermore, the WID 125 can include a trackpad, mouse and/or mouse pad 425, such as those typically found on laptop computers. The trackpad, mouse and/or mouse pad 425 may also include one or more buttons to enable the selection of an item on the screen 405. It should also be appreciated that although the WID 125 is illustrated as similar to a tablet computer, the WID 125 may include a smaller handheld device, such as a Personal Digital Assistant (PDA), or a larger device such as a large plasma screen.

III. WID Function

FIG. 5 is an illustrative partial view of a hospital 500 in which the system of the present invention operates, according to one embodiment of the present invention. The hospital 500 includes a ground-based tracking system that includes a plurality of indoor communication units 505 that receive RF or other signals transmitted by the WID 125 as it moves through the hospital 500, which are in turn used to accurately identify the position of the WID 125. As illustrated in FIG. 5, these communication units are preferably located in every room, including patient rooms 510, 520, 530, 540, facilities rooms 550, pharmacy rooms 560, nursing stations 570, laboratories 580, in other rooms (e.g., operating rooms), and in hallways 545, to provide accurate positioning information for the WID 125 as it moves through the hospital 500.

As shown in FIG. 5, patients 508, 516, 518, 528, 538 reside in patient rooms 510, 520, 530, and 540. Each patient 508, 516, 518, 528, 538, in turn, is associated with a smart card, RF Tag or barcode 509, 517, 518, 529, 539. Alternatively, as discussed above, each patient 508, 516, 518, 528, 538 may be associated with a GPS receiver/transmitter or like location-identifying device (e.g., an active RF tag), to identify their location to the ground-based tracking system. The WID 125, as it moves through the hospital 500 can wirelessly communicate with a hospital server 555, which is capable of serving facility and patient information to the WID 125, as well as receiving information from the WID 125. According to one aspect of the invention, the hospital server 555 resides in a computer room 550 of the hospital 500. According to another aspect of the invention, the hospital server 555 may be located remote to the hospital 500. According to yet another aspect of the invention, the hospital server may include a number of computers that collectively perform the functions of the server described herein.

Significant pieces of equipment 525, 535 (e.g. CT-scanner, anesthesia cart in an operating room, specialized infusion pumps that deliver high risk infusions, such as chemotherapy, blood products, etc.) in the hospital 500 may also be in communication with the hospital server 555. Where these devices are in active communication with the server 555 (i.e., they update their location to the server 555 using GPS transmitters, active RF tags, hardwire links or the like) they may be cross-referenced to patient locations to ensure the correct patient is given the correct treatment. Alternatively, these devices may only have smart cards or barcodes to enable the WID 125 to identify them when in their vicinity.

The hospital server 555 receives information input into one or more databases from hospital computers 558*a*, 558*b*, 558*c*, and 558*d*, which respectively may represent computers used to receive or generate accounting data, pharmacy data, patient data, and lab data. Therefore, each of the hospital computers 558*a*, 558*b*, 558*c*, and 558*d* are preferably in hardwired electrical communication with the server 555 via a local area network (LAN) or wide area network (WAN) so as to download information for storage and retrieval by the hospital computer system. Next, the use of the WID 125 will be described in the context of the illustrative partial-view of the hospital 500.

A. WID User Sign-In

Upon picking up a WID 125, a user must initially turn on the WID 125 and verify their identity. As described above, the WID 125 is capable of automatically identifying users carrying a smart card, RF tag, or barcode. However, if one of those items is lost or stolen, a person that should not have access to medical records could pick up the smart card, RF tag or barcode and attempt to access secure medical information via a WID 125. As a result, additional security measures may be warranted. More particularly, each WID 125 may require that a user manually input a password prior to obtaining rights to use the WID 125. This may ensure that the device, in addition to secure communications transmitted to the device, are HIPAA compliant.

The password is compared to the user's smart card (or RF Tag or barcode) and with the user's password as stored on the hospital server 500, to verify the identity of the user. This log in process may occur at the beginning of each day. Alternatively, the WID 125 may require manual password entry at random times throughout the day, even while the physician is logged on, flagging possible theft and unauthorized use of the WID 125 should the proper password not be detected. Furthermore, a switch may be incorporated onto the WID 125 to force it into a mode requiring password entry. The transmission of passwords to the server may be security by encryption keys, as are well known in the art, to prevent their being discovered.

More elaborate means, including voice identification or a fingerprint or retinal scan, may also be incorporated into the WID 125 to reinforce such security. For instance, instead of having a conventional password log-in the WID 125 may include a finger print pad to confirm a user's identity. The finger print pad must be capable of discerning the characteristics of a fingerprint when a thumb is pressed thereon. Various systems for discerning fingerprint characteristics have been provided in the prior art and therefore will not be explained here in detail. Suffice it to say that any method for discerning characteristics may be used here which can be implemented in a relatively small electronic package. The finger print pad is linked to the WID application 315, and the print characteristics are transmitted to the server 555 for interrogation.

According to another embodiment of the present invention, if each healthcare worker is associated with a particular WID 125, when an WID 125 is initially provided to a healthcare worker the healthcare worker may commission the WID 125 by placing his or her thumb on the finger print pad a first time. During a commissioning protocol, the first time a thumb is placed on the pad, the WID application 315 may discern fingerprint characteristics and stores the discerned characteristics in the WID memory 310. In addition to storing fingerprint characteristics, the WID application 315 may be equipped with code for comparing fingerprint characteristics and based on the comparison, for either allowing the WID 125 to be used or disabling the WID 125. In this embodiment, prior to the WID 125 being used for any information gathering, transmitting, generating or interrogating purposes, a healthcare worker must place his or her thumb on the finger print pad. The above alternative embodiment is beneficial where healthcare workers do not wish to give up control of their biometric indicia to the hospital for storage on the hospital server 500. It will also be appreciated that although the fingerprint ID verification process is described above, ID verification using the WID 125 of the present invention may also be effected by any other recognizable biometric indicia or uniquely personal biomedical indicia. For example, a retinal scanner or voice recognition identifier could be used to verify a person's identity.

A user-log-in process to the WID 125 is illustrated in block diagram form in FIG. 6. As shown in FIG. 6, after a user picks up and turns on a WID 125 (block 600), the user may be identified via one of three methods: (1) by a manually input user ID (block 615); (2) by the WID 125 querying the user's smart card or RF tag, or reading the user's barcode for identification (block 610); or (3) by identifying the user based on the user's thumbprint or other biometric data (block 620). After any of the above three (3) steps are completed, the WID 125 then confirms the user's identification with the hospital server 555 by comparing the received ID information with that stored in a security file (block 625).

The WID 125 also queries the user for a password (block 625), which is preferably input by the user (block 630) using the WID's touch screen. As described above, this prevents fraud when a smart card, RF Tag or barcode is lost or stolen. After the user inputs his or her password (block 630), the WID 125 either compares the password with the correct password transmitted to it from the server 555 (block 632), or transmits the password to the server 555 for comparison to the correct password as stored in the hospital security file (block 632). If the password is incorrect the user's identity is reconfirmed and the user is asked for his or her password again (block 625). Although not illustrated in the block diagram flow chart of FIG. 6, after a predetermined number of unsuccessful login attempts, the WID 125 may shut down or lock to prevent further login attempts. According to another aspect of the present invention, after a number of consecutive unsuccessful login attempts the WID 125 may also report the login attempts to hospital security personnel via email in an effort to identify potential fraud.

On the other hand, if the password is correct the WID 125 performs a handshake with the ground-based tracking system to determine the WID's location (block 633), after which the WID 125 uploads the user-customized format based on user-defined rules (block 635), as explained further below with respect to FIG. 8. The WID 125 then uploads location-based customized content and displays the content in the user-customized format (block 640). According to one embodiment of the present invention, because thumbprints or other biometric input are highly reliable forms of identification, a user may not be queried for a password in some embodiments of the present invention, as is illustrated in FIG. 6. Therefore, after providing a thumbprint or biometric input, the WID may confirm the user's ID with the server 555 based solely on this information (block 626), after which the WID 125 performs a handshake with the tracking system to determine its location (block 633). After log-in, a user is prepared to utilize the features of the WID 125.

B. Context-Relevant Information and User-Customized Interfaces

FIG. 7A shows the path of a user associated with a WID 125 in the illustrative partial view of the hospital 500 shown FIG. 5, according to an illustrative example of a method and system of the present invention. In the illustrative example of FIG. 7A, a WID-user physician logs into the WID 125 immediately after entering the hospital 500. After logging in using the one of the processes described in detail above with respect to FIG. 6, the ground-based tracking system identifies the physician's location 710 in the hallway 545 through the use of one or more indoor communication units 505 that receive RF or other signals transmitted by the WID 125 as it moves through the hospital 500.

Upon the physician's log-in the WID 125 immediately receives context-relevant information for display to the physician. In particular, the information served to the physician via the WID 125 is information the physician wishes to view for the context the physician is currently in. Furthermore, the information is displayed according to predefined display rules established by the physician. The identification, retrieval, and display of context-relevant and customized information is explained in detail with reference to FIG. 8 below.

FIG. 8 is a block diagram flow chart illustrating how the WID 125 serves context-relevant information to users, and displays the information to the users in customized formats established by the users according to one embodiment of the present invention. As shown in FIG. 8, a user is initially logged into the WID 800 (block 800) using one of the techniques discussed above with respect to FIG. 6. Log-in identifies the user to enable the WID 125 to serve relevant information to the user. After log-in, the ground-based tracking system identifies the location of the WID 125 and reports the location of the WID 125 to the server 555 (block 805). Additional information that may be reported to the server 555 are the identities and/or locations of persons, such as patients, and objects, such as hospital equipment, in communication with the WID 125. As explained in detail above, these persons and objects may be identified by the WID 125 using smart cards, RF Tags, barcodes, and the like.

Next, the server 555 identifies the context of the WID 125 (block 810) based on the WID's location and/or persons or objects in communication with the WID 125. More specifically, the WID's context identifies the environment in which the WID exists, typically relative to a logged-in user. For instance, a context may be that the WID 125 is in the presence of a physician visiting a patient in a patient room, or that the WID 125 is positioned in the operating room in which a patient's surgery is being performed. Other illustrative contexts may be that the WID 125 is in the possession of a nurse visiting a patient, or in the possession of a physician in a doctor's lounge. As a specific example, the server 555 may identify that a WID 125 is associated with a particular physician (identified by the physician's log-in to the WID 125) who is in the presence of a patient, as identified by the patient's RF Tag, where both the physician and patient are in the patient's room. It will be appreciated that the above examples are intended to be illustrative and non-limiting examples, and that the WID 125 may experience a large variety of environments, and thus, contexts.

Next, the server 555 applies a user's predefined information rules to determine what context-relevant information is served to the WID 125 in any particular context as the WID 125 (block 815). These predefined information rules also include predefined display rules, such that after the appropriate information for transmission to the user's WID 125 is identified, the information may be presented in a format requested by the user. In this manner, each user can not only define the type of information he or she wishes to view for a particular context, but also the format in which that information is presented. FIG. 8 illustrates, in part, a particular user's predefined information rules (hereafter referred to as information rules) 845, which are associated with the particular user as identified by a user ID 830.

As shown in FIG. 8, information rules, such as information rules 845, are preferably stored in the one or more database(s) illustrated in FIG. 1 and accessible by the server 130. In the illustrative example shown in FIG. 8, the information rules 845 contain a plurality of contexts, each of which are defined by a context definition. Two contexts illustrated in FIG. 8 are default 835, and patient room 840 (illustrated in part). The context definitions, shown in the header of the illustrative contexts 835, 840, are defined relative to the location of the WID and the interaction of the WID with objects (e.g., patients). Because each context is also defined for a particular user (defined by user ID 830), the context definitions define the context relevant information provided to a specific user associated with a WID at a specific physical location, and the user's proximity to other people and objects.

For instance, the patient room 840 context may be invoked according to a context definition that defines that this context exists whenever the user (holding the WID 125) is in a patient's room and in the presence of a particular patient. Various contexts may be defined using the information rules 845, such as an Operating Room, a Lab Room, an X-Ray Room, etc. According to the illustrative embodiment of FIG. 8, a default 835 context may exist when no other contexts are applicable. For instance, where a physician has just entered the hospital and has yet to interact with patients, a default 835 context may be appropriate.

Referring to the default 835 context in FIG. 8 as an illustrative context, the information rules 845 define display fields within the default, including: basic information, ID, patient list, new data, patient messages, patient alerts, hospital messages, and miscellaneous notifications. Each one of these fields represent information that the particular user 830 wishes to view in the default context. Furthermore, each of the fields include the content displayed with that field, along with display information that establishes how the content is displayed to the user. For instance, in the default 835 context, there is a basic information field that will instruct the WID 125 to display the hospital name in the position and in a size defined within the basic information field.

Because each user has their own predefined list of contexts, and may customize the information served to their corresponding WIDs in each context, as well as the format in which it is presented, each user may receive highly customized information via their WID. For instance, the default 835 context for a first user may include a patient alerts field, whereas a default 835 context for a second user may not contain such a field. As discussed further below, the context definitions, display fields, and content therein may be changed by a user on a real-time basis, so that the information rules 845 may be altered at any time by a user. However, according to one aspect of the present invention, changing the information rules 845 may require authorization from a system administrator, or may not be allowed to prevent users from changing pre-set information rules 845. After the server applies a user's information rules for a particular context (block 815), the server collects the facility and patient information identified by the information rules (block 820), and then transmits the information to the user's WID 125 for display.

Referring to FIG. 7B, it will be appreciated that a WID 125 of the present invention may accompany a user, such as a physician 710, standing in a first room 753 in the presence of a first patient 755. Although the WID 125 is in the presence of the first patient 755, the WID 125 may actually be physically closer to a patient in another room, such as patient 765 in second room 763. As illustrated in FIG. 7B, distance A 760 is therefore greater than distance B 770. It will also be appreciated by those of ordinary skill in the art that this scenario could occur with items on separate floors, where the WID 125 is closer to an item on the floor above it than an item in the same room with the WID 125.

Where both patients are associated with the user of the WID 125, to prevent the WID 125 from displaying the patient information for the second patient 765 in the second room 763, the server 555 may serve information to the WID 125 based on a default that serves information to the WID 125 only for patients in its line of sight or within the same room. This may be established by the server 555, which knows the respective locations of the WID 125, patients 755, 765, and can map each in relation to a hospital floor plan. More specifically, the server 555 may operate based on rules, such as the fact that the WID 125 will not receive information corresponding to objects and persons on the other side of a wall, on a different floor, or outside of a room in which the WID 125 is located. According to one aspect of the invention, the distance of each object from the WID 125 is ranked and placed in a queue, where the distance is determined based on the distance the WID 125 would have to move to be at the location of the second object (thus taking into account walls and floors). The closest object may initially be the subject of the WID display. These rules may be a default rule for automatic display of information, and may be overridden by the user using the WID interface, described in detail below.

According to one aspect of the invention, the WID 125 must also be in the presence of a person or object for a minimum amount of time, configurable by the user, before information associated with that person or object is displayed. This may prevent the WID 125 from 'jumping', or switching in between displays, where the user passes multiple persons or objects, as in the event where a physician or nurse passes multiple patients in the hallway 545 in rapid succession. According to another aspect of the invention, the WID 125 may offer the user a choice between patients, or may require an acceptance (e.g., by stylus selection on the touch-sensitive screen) before information for a different person or object is displayed. This may permit a doctor making rounds to continue viewing information associated with one patient without interruption and concern that the display will automatically switch to a different patient. However, according to yet another aspect of the present invention, the WID 125 may permit information corresponding to two patients to be viewed simultaneously using a split screen display, or may open successive graphical windows in the display, where each window is associated with a particular patient or object.

An illustrative example of the WID's 125 display as a physician enters the hospital at location 710 of FIG. 7A, is shown in FIG. 9. For purposes of illustration, the information displayed by the WID 125 FIG. 9 correspond to the default 835 context illustrated in FIG. 8. As shown in FIG. 9, the WID 125 display 905 includes a basic information field 920, located in the upper left hand corner of the WID 125 shown in FIG. 9, which may provide basic information about the user's location. In the illustrative example of FIG. 9, the WID 125 displays the hospital name, along with a welcome message. As shown in FIG. 8, the location of this field, and the identification of the hospital name, are established by the user's information rules 845. As shown in FIG. 9, the WID 125 may also present the user's ID 925 on the display 905, along with a picture 935 of the physician, to confirm that the physician is accurately logged into and identified by the WID 125. According to a preferred embodiment of the present invention, the picture 935 is presented in color.

Also presented on the display 905 are fields including a patient list 940, new data 930, patient messages 945, and patient alerts 950. These fields provide basic information to the physician relating to the physician's patients. For instance, the patient list 940 includes a list of all of the physician's patients, along with their respective room numbers and primary physician. Although the patient list 940 in FIG. 9 only shows three patients, due to the real-estate available on the screen 905, additional patients may be viewed by the physician by pressing or selecting the down arrows in the patient list 940. Pressing the down arrows scrolls the list to display additional information. This feature may be used to display additional information in any of the fields discussed herein, though not illustrated.

The new data field 930 may indicate any new data associated with the physician's patients, including the date of the new data, the patient name associated with the new data, and a brief summary of the type of new data available. This new data may be displayed to the physician depending on how recent the new data is. According to one aspect of the invention, the new data may be displayed at least once on the WID 125 and removed only be selection of the physician, to ensure that the physician views all of the new data in the new data field 930. According to another aspect of the present invention, the physician may select one of the new data entries to obtain an expanded view of the new data entry, with all of the information related to the new data. This expanded view may pop up in a separate window that replaces some or all of the fields 940, 930, 945, 950, 955, 960, or may pop up in a window that is superimposed on the display shown in FIG. 4. To return to the display shown in FIG. 9, or to close the superimposed window, the physician may be instructed to select a close button. These graphical user interface (GUI) features are implemented by the WID application 315 discussed above with respect to FIG. 3.

The alerts field 950 is similar to the new data field, but may contain only data and information indicated as abnormal, either by other physicians, nurses, lab technicians, or hospital equipment. Therefore, abnormal data may be flagged and automatically presented in the alert field 950. As with the new data field 930, each alert contains a brief summary and is associated with a particular patient. Also like the new data field 930, the physician may be able to expand each alert entry to view additional information.

The display 905 may also contain a patient messages field 955 that displays patient-related messages, including the identification of the person leaving the message, and a brief summary of the message. As with the other fields, each of the entries can be selected via the touch-screen or via a keyboard or mouse, such that the entire messages may be viewed or listened to, in the case of recorded messages, using the WID's speakers. Additional fields include hospital messages 955 and miscellaneous notifications 960, which may respectively include general hospital messages and various notifications, such as medical news.

As is also shown in FIG. 9, there is at least one navigation tool 965 that permits a user to manually change the context and thus display of the WID 125, or to selectively view information corresponding to patients or the hospital. Other toolbars not illustrated may also be used, including those that permit a user to access calendars, schedules, directories, and other information that may not be context specific, but which may aid the user in practice administration. The toolbar(s) may be established by the information rules 845, or by the WID application 315. Preferably the toolbar(s), like the context-relevant information displayed by the WID 125, are configurable by a user and established by the information rules 845. Also displayed for the user's convenience and to evidence that the WID 125 is in communication with the server 125 is a display of the date and time 970.

Next, FIG. 10 is a block diagram flowchart showing the transmission of facility and patient information to the WID 125 as a user enters a patient room via the path shown in FIG. 7A. In this example, after a user-physician has logged into the WID (block 1000), the physician may enter 720 a patient room 520, which includes two patients 516, 518 each associated with a smart card, RF tag or barcode 517, 519. Upon entering the patient room 720, the ground-based tracking system identifies the physician's location (block 1020).

According to one aspect of the present invention, the WID 125 may automatically receive patient information from the server 555 upon entering the patient room 520. Therefore, the location of the WID 125, rather than the presence of the WID 125 adjacent to or near a patient, may trigger a patient room 840 context. For instance, as shown in FIG. 10, after identifying that the user is in a patient room (block 1020), the server 555 may access hospital records and identify the patient assigned to the room in which the WID 125 is located (block 1022). Afterwards, patient information associated with the patient assigned to the room may be transmitted to the WID 125 for display to the user (block 1024). Where the patient room is associated with a single patient, the patient information may automatically be displayed. However, where there are two or more patients in the room, the server 555 may cross check both patients against the physician's patient list to determine which patient the physician is visiting. Alternatively, the user may be asked to select between the two patients via a pop up selection, as is known in the art.

As an alternative to the automatic triggering of a patient information based on the fact that the user-physician enters a particular room, the systems and methods of the present invention may serve patient information associated with a patient located closest to the WID 125. For instance, referring again to the path of a physician in the partial view of the hospital 500, upon approaching a patient 730 the WID 125 may query the patient's smart card, RF tag or barcode (or manually input the patient ID) (blocks 1023, 1025). According to one embodiment of the present invention, the WID 125 will only receive information on a user or object with which the WID 125 is in wireless communication after access to the patient information is authorized by the server.

According to one aspect of the invention, the WID 125 must also be in the presence of a person or object for a minimum amount of time, configurable by the user, before information associated with that person or object is displayed. This may prevent the WID 125 from 'jumping', or switching in between displays, where the user passes multiple persons or objects, as in the event where a physician or nurse passes multiple patients in the hallway 545 in rapid succession. According to another aspect of the invention, the WID 125 may offer the user a choice between patients, or more require an acceptance (e.g., by stylus selection on the touch-sensitive screen) before information for a different person or object is displayed. This may permit a doctor making rounds to continue viewing information associated with one patient without interruption and concern that the display will automatically switch to a different patient. The WID 125 may also permit information corresponding to two patients to be viewed simultaneously using a split screen display, or may open successive graphical windows in the display, where each window is associated with a particular patient or object.

Referring once again to FIG. 7A, where the first patient 518 is not the user-physician's patient, the server 555 will not display information associated with the first patient 518 on the WID 125 because the server compares authorization rights of the logged-in user to information served to the WID 125 under the context rules described above with respect to FIG. 8. For instance, if the first patient's identification does not match the identification of any patient on the physician's treatment list, as compared by the server 555, the WID 125 will not display patient information for the first patient 518. Therefore, upon approaching 730 the patients 516, 518, the physician may only receive patient information for the second patient 516.

Figure 11:
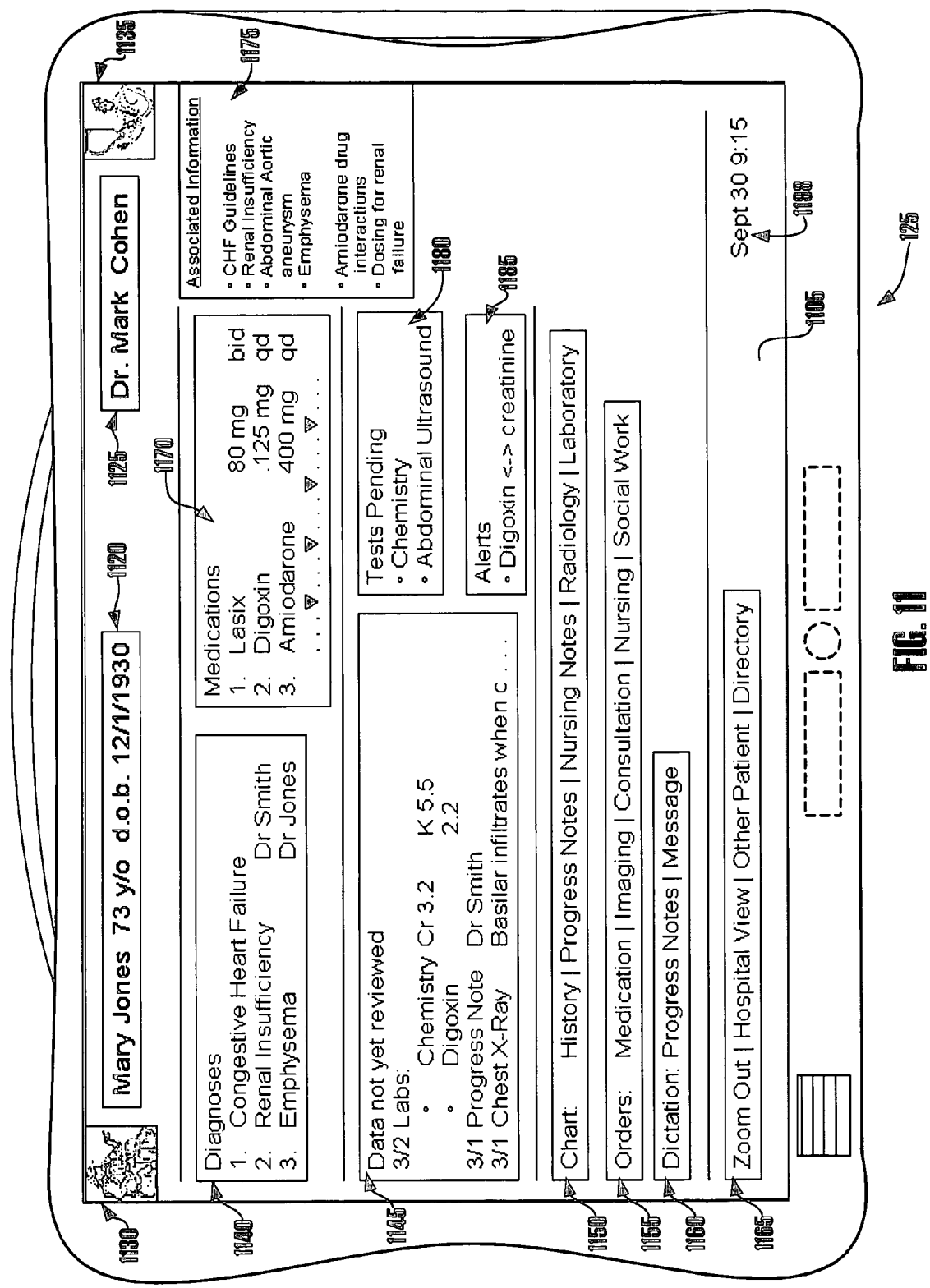

FIG. 11 shows an illustrative example of the WID 125 as a user-physician visits with the second patient 516 in FIG. 7A, according to an illustrative example of the present invention. In particular, the WID 125 of FIG. 11 shows a patient room context, where basic patient information 1120 is illustrated in the upper leftmost corner of the display 1105. As illustrated, the patient information 1120 may be presented along with a picture 1130 of the patient to confirm that the appropriate patient's information is being displayed. As was shown in FIG. 9, the WID 125 may also present the user's ID (here, the user's name) 1125 on the display 1105, along with a picture 1135 of the user, to confirm that the user is accurately logged into and identified by the WID 125. According to a preferred embodiment of the present invention, the pictures 1130, 1135 are presented in color.

Also presented on the display 1105 are fields including diagnoses 1140, medications 1170, tests pending 1180, alerts, 1185, associated information 1175, and data not reviewed 1145. These fields provide basic information to the physician relating to the physician's patient. For instance, the diagnoses field 1140 includes a list of all of the diagnoses of the patient, along with an identification of who is managing the diagnosis. Likewise, the medications field 1170 shows all of the medications the patient is on, along with amounts and form. As with the fields in FIG. 9, additional medications may be viewed by the physician by pressing or selecting the down arrows in the medications field 1170. Pressing the down arrows scrolls the list to display additional information.

The data not reviewed field 1145 may indicate any new data associated with the patients, including the date of the new data, a short summary or description of the data, and the name of the person, if any, providing the data. The new data may be displayed to the physician depending on how recent the new data is. According to one aspect of the invention, the new data may be displayed at least once on the WID 125 and removed only be selection of the physician, to ensure that the physician views all of the new data in the data not reviewed field 1145. According to another aspect of the present invention, the physician may select one of the new data entries to obtain an expanded view of the new data entry, with all of the information related to the new data. This expanded view may pop up in a separate window that replaces some or all of the fields, or may pop up in a window that is superimposed on the display shown in FIG. 11. To return to the display shown in FIG. 11, or to close the superimposed window, the physician may be instructed to select a close button. These graphical user interface (GUI) features are implemented by the WID application 315 discussed above with respect to FIG. 3.

The alerts field 1185 is similar to the data not reviewed field 1145, but may contain only data and information indicated as abnormal, either by other physicians, nurses, lab technicians, or hospital equipment. Therefore, abnormal data may be flagged and automatically presented in the alert filed 1185. According to one aspect of the present invention, when posted new alerts may flash for a brief period of time, or until selected by the user (e.g., by pressing the alert) to ensure they are viewed. The display 1105 may also show a tests pending field 1180, which shows a brief summary of all tests pending for the patient. Additionally, the display 1105 may include an associated information field 1175 that includes miscellaneous information associated with the patient or the patient's conditions.

As with the fields described with respect to the example of FIG. 9, each of the entries can be selected via the touch-screen or via a keyboard or mouse, such that the entire messages may be viewed or listened to, in the case of recorded messages, using the WID's speakers. Furthermore, as with all of the displays discussed herein, a user can increase or decrease the size of each field, in the same manner as in Microsoft Windows™ GUIs. The user may also drag the fields around the screen to reposition the fields. According to one aspect of the invention, the fields will overlap. According to another aspect of the invention, the fields will not overlap, so that the increase in size of a first field may reduce the size of an adjacent field. Additionally, the user can select each field's font, via a right click on a selection button after the field is chosen via the stylus, or by like means as are well known in the art. According to yet another aspect of the invention, a physician can remove fields by closing them, which may occur by dragging them to a trash bin (not illustrated), or by similar means known to those of skill in the art. Once any changes in the screen display are made, the changes are transmitted (either after each change, or periodically) by the WID 125 to the server 555, where the changes are stored in the information rules, and more specifically, the display fields for each context element.

As is also shown in FIG. 11, there are multiple navigation tools 1150, 1155, 1160, 1165 that permits a user to manually change the display of the WID 125, or to selectively view information corresponding to patients or the hospital. Other toolbars not illustrated may also be used, including those that permit a user to access calendars, schedules, directories, and other information that may not be context specific, but which may aid the user in practice administration. The toolbar(s) may be established by the information rules 845, or by the WID application 315. Preferably the toolbar(s), like the context-relevant information displayed by the WID 125, are configurable by a user and established by the information rules 845. Also displayed for the user's convenience and to evidence that the WID 125 is in communication with the server 125 is a display of the date and time 1198.

The display 1105 described with respect to FIG. 11 may be shown while the physician visits the patient 516 (block 1030), at which time the physician may use the WID 125 to enter additional patient information. This may be done using dictation, as described above, the WID keyboard, drop down lists for medications, diagnoses, or for any other field displayed on the WID 125, or using handwritten notes on which the WID or server 555 can perform optical character recognition. Other inputs, such as photographs, may also be input if the WID 125 includes additional input/output features (such as an integrated digital camera). Any input entered by a physician is transmitted to the server 555, which is operable to interpret the type of information received and to update any and all databases accordingly. As a result, information entered into the WID 125 is disseminated immediately to any source that may require the information.

Figure 12:
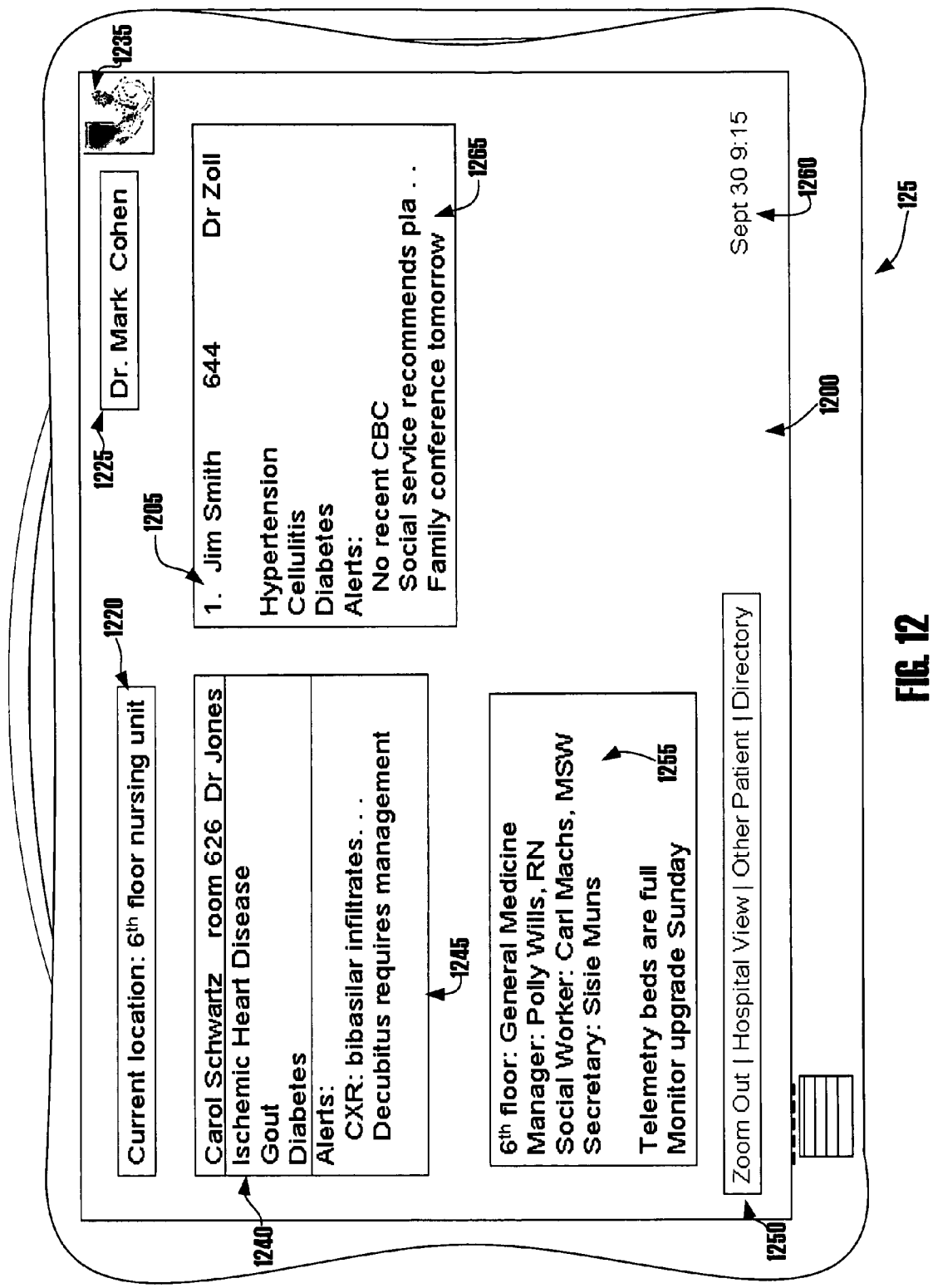

Next, FIG. 12 shows an illustrative example of the WID 125 when a user-physician holds the WID 125 in a hospital nursing unit, according to an illustrative example of the present invention. As shown in FIG. 12, along with a basic information field 1120 (here, showing the location of the WID), and user ID 1225 and picture 1235 fields, as described above. In this context, the WID 125 display 1200 shows information on the user-physician's patients on the floor in individual fields 1205, 1240, along with a detailed location information 1255 field displaying general information about the nursing unit. At least one individual patient field 1240 also includes an alert field 1245, as described above with reference to FIG. 11.

As with the other illustrative displays described herein, all elements shown in the respective fields 140, 145, 1255, 1265 are selectable should the user with to view additional details. For instance, to view additional details or an expanded view of a particular patient, the patient's field may be selected. According to one aspect of the invention, this may result in the display 1200 changing to the patient room context display described above with respect to FIG. 11.

Figure 13:

FIG. 13 shows another illustrative example of the WID 125, when the WID is utilized as a fixed display in a hospital operating room (OR). In this embodiment, the WID 125 may be a large wall mounted display, such as a large plasma or LCD screen. The WID 125 displays context relevant information needed by a physician surgeon and an operating team. Therefore, in addition to a basic information field 1300 that displays the patient's name, and a patient picture field 1310, information is also displayed in fields 1330, 1335, 1340, 1345, 1350, 1355, 1360, 1365, 1370, 1380 that describe the surgery, surgeon(s) and staff, anesthesia, pertinent patient information or conditions, and/or additional information.

When undergoing an operation, the operating room anesthesia cart can be wired into the hospital server 555. Thus, the server 555 knows which patient is laying on the table via the patient smart card, RF tag or GPS device. The display in the OR may show the patient name, operation scheduled, medications, allergies, physician scheduled, problem list, etc., as provided by the server 555 based on the hospital records and the patient located in the operating room Thus, the display can indicate if the wrong patient is in the operating room. Therefore, communication from the pre-op anesthesiologist evaluation to the OR will be error free and seamless when utilizing the systems and methods of the present invention. It will thus be nearly impossible to operate on the wrong leg, or administer a medication the patient is allergic to.

Figure 14:
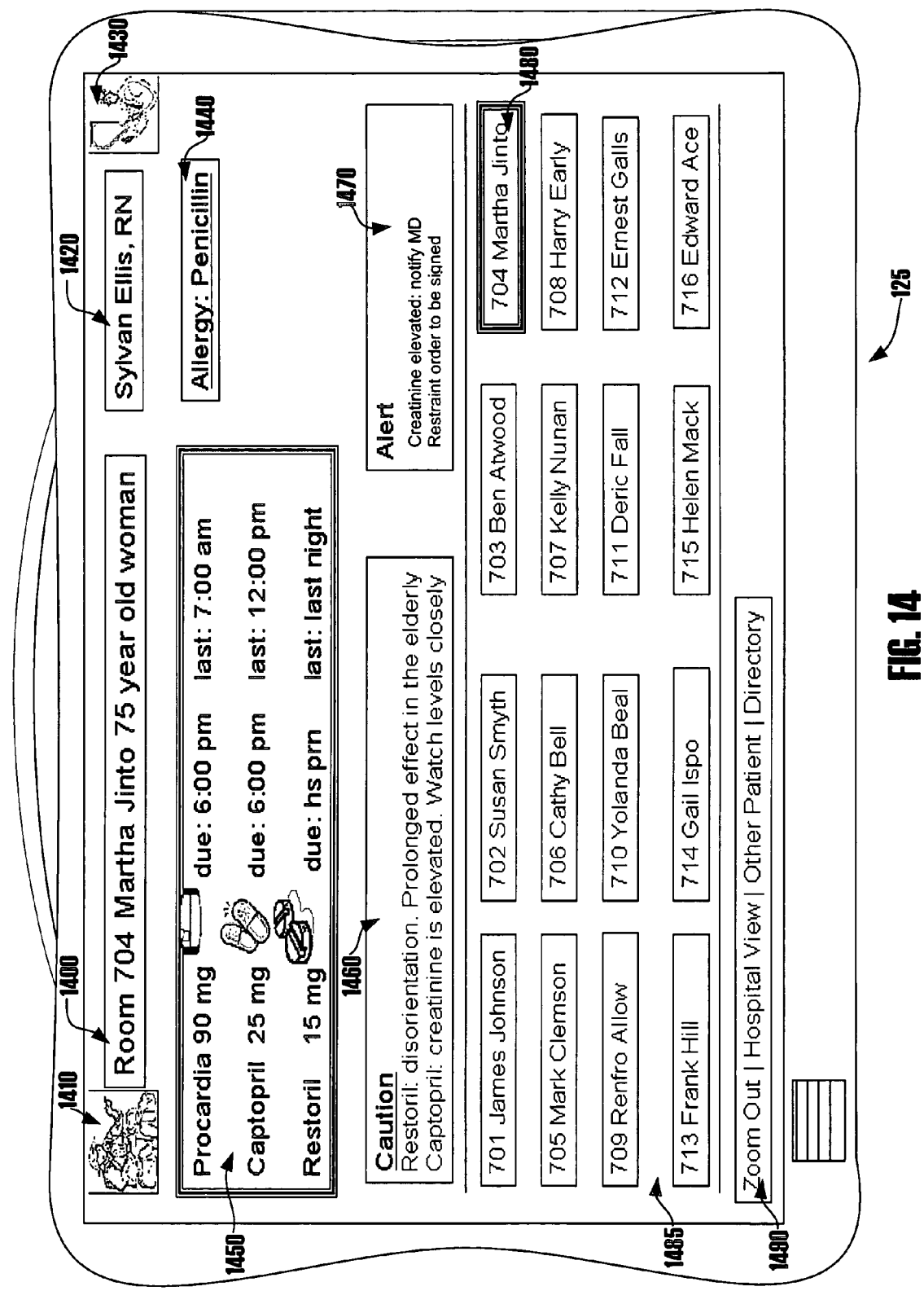

Yet another illustrative example of a WID 125 is shown in FIG. 14. In this example, the user is a nurse preparing medications for distributing to patients. Therefore, the WID 125 is displaying a medication preparation screen, which may be selected by a nurse manually via one or more navigation tools on the bottom of the WID 125 screen. According to one aspect of the present invention, the WID 125 may accompany or be integrated with a tray in which pills are distributed in compartments. The tray may be filled by the nurse, who may select each patient to view the appropriate set of medications.

As shown, the patient identification field 1400 includes the name and basic information on the patient, next to a picture 1410 of the patient. The user ID 1420 and picture 1430 fields of the nurse associated with the WID 125 are also displayed. Below the patient identification field is a graphical medication field 1450, which shows the medications the patient takes, along with the dose, a picture of the medication, time next medication is due, along with the time the last medication was administered. Pictures of the medication are added to provide confirmation of the medication so as to reduce the likelihood of error in medication dispensing. An allergy field 1440, warning or caution field 1450, and alert field 1470 are also provided. The WID 125 display also shows the names of the user-nurse's patients on the floor in individual fields 1485, each of which may be selected to show the medication preparation screen for the respective patients. Additionally, as with the other screens, one or more navigation fields 1480 permit the user to navigate through the information provided by the WID 125.

Figure 15:
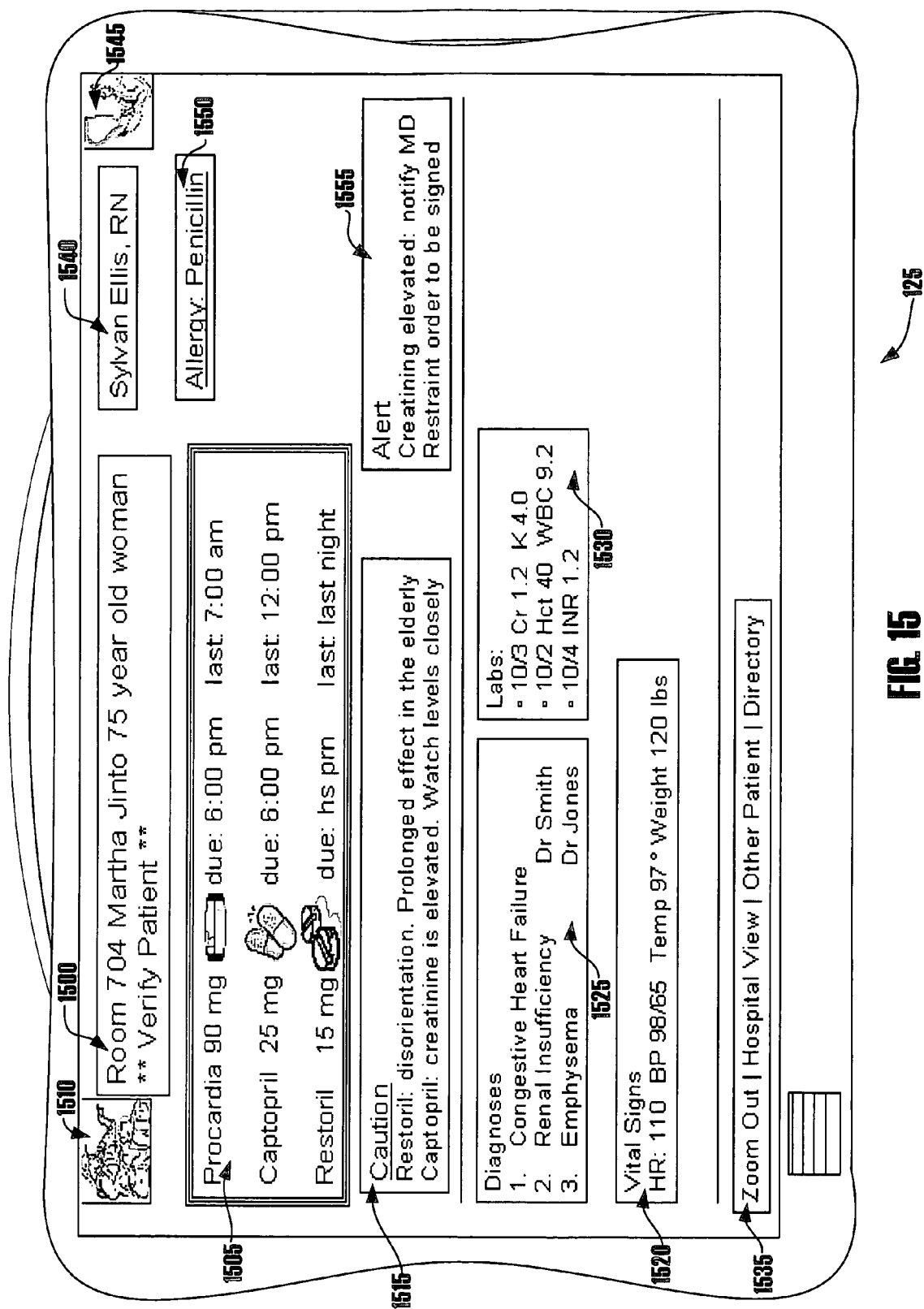

FIG. 15 shows an illustrative example of a WID 125 screen that may be displayed while the nurse delivers medications. The screen includes some of the same fields as that display shown in FIG. 14, such as the patient identification field 1500, patient picture 1510, user ID 1540 and picture 1545 fields, graphical medication field 1505, allergy field 1440, warning or caution field 1450, alert field 1470, and navigation field 1535. Additional fields include a diagnoses field 1525, lab field 1530, and vital sign field 1520, which may identify conditions that may impact the dispensing of medication to a particular patient. As described above, the patient information for the patient positioned closest to the nurse may be brought up automatically.

It will be appreciated that the context relevant information examples discussed above are illustrative and not limiting. The system of the present invention is capable of providing context relevant information in a variety of situations. As another example, the taking of vital signs is nearly uniformly done by a combined blood pressure, heart rate, and temperature device located on a rolling pole. With the server 555 knowing the location of the pole, and the location of a patient, the information from the pole may be transmitted directly to the electronic chart. This may be done even without the WID such that there is no clipboard, no transcription errors, nor time-lag from the acquisition of the data to the distribution of the data.

While the present invention is described above in the context of a hospital, it is equally within the scope of the present invention to apply a substantially similar system for the tracking, retrieval and presentation of data in other context, such as hotels, resorts, cruise ships, schools, manufacturing facilities, or virtually any place where contextually relevant data is desirable. For instance, in the context of a hotel, the house keeper could have a wireless tablet that displays occupant-relevant data as the house keeper enters each room, such as a standing request from the occupant for additional towels.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for serving context-relevant information in a healthcare facility, comprising:

identifying, by a healthcare information server, a user associated with a wireless information device;

determining, by the healthcare information server, that the wireless information device is in a first room in the healthcare facility;

determining, by the healthcare information server, that a first person is in the same first room at least in part by querying at least one healthcare database based on the identity of the first room;

determining, by the healthcare information server, that a second person is in a second room, wherein the wireless information device is physically closer to the second person than to the first person;

selecting, by the healthcare information server, the first person for retrieving and transmitting information associated therewith by comparing the proximity of the first person and the proximity of the second person to the wireless information device and selecting the first person based upon determining that the first person is in the same first room as the wireless information device;

determining, by the healthcare information server, that at least one object is located in the first room at least in part by querying the at least one healthcare information database based on the identity of the first room and based on an association of the first room with the first person;

retrieving context-relevant content from at least one healthcare database, wherein the context-relevant content comprises information about the first person, information about the first room, and information about the at least one object, wherein the information about the first person comprises at least one of: medication information, diagnosis information, healthcare specialty information, or patient history information;

limiting the context-relevant content based at least in part on the identity of the user and user preferences associated with the user and stored in the at least one healthcare database;

transmitting the context-relevant content from the healthcare information server to the wireless information device at least part of which is used to automatically generate a presentation to the user via the wireless information device, wherein the presentation comprises the information about the first person, the information about the first room, and the information about the at least one object.

2. The method of claim 1, wherein the step of identifying a user comprises identifying the user based on a device associated with the user.

3. The method of claim 1, wherein the step of identifying the user comprises identifying the user based on biomedical indicia of the user.

4. The method of claim 1, wherein the at least one object is selected from a group of objects consisting of a person, a room, and equipment.

5. The method of claim 1, further comprising automatically presenting at least a portion of the context-relevant information to the user via a display of the wireless information device.

6. The method of claim 5, wherein the step of automatically presenting at least the portion of the context-relevant information further comprises the step of automatically presenting at least the portion of the context-relevant information to the user based on display rules.

7. The method of claim 6, wherein the display rules are stored external to the wireless information device.

8. The method of claim 6, where the display rules are established, at least in part, by the user.

9. The method of claim 1, wherein the step of determining that the wireless information device is in the first room comprises determining the location of the wireless information device using a tracking system selected from the group of tracking systems consisting of a global positioning system and a radio frequency-based positioning system.

10. The method of claim 1, further comprising determining, by the server, that the first room is on a first floor and that the second room is on a second floor.

11. A system for displaying information, comprising:
at least one healthcare database;
a wireless information device, the wireless information device being associated with a user; and
at least one healthcare information server, in wireless communication with the wireless information device and the at least one healthcare database, wherein the at least one server is operable to:
  identify a user associated with a wireless information device;
  determine that the wireless information device is in a first room in the healthcare facility;
  determine that a first person is in the same first room at least in part by querying the at least one healthcare database based on the identity of the first room;
  determine that a second person is in a second room, wherein the wireless information device is physically closer to the second person than to the first person;
  select the first person for retrieving and transmitting information associated therewith by comparing the proximity of the first person and the proximity of the second person to the wireless information device and selecting the first person based upon determining that the first person is in the same first room as the wireless information device;
  determine that at least one object is located in the first room at least in part by querying the at least one healthcare information database based on the identity of the first room and based on an association of the first room with the first person;
  retrieve context-relevant content from at least one healthcare database, wherein the context-relevant content comprises information about the first person, information about the first room, and information about the at least one object, wherein the information about the first person comprises at least one of: medication information, diagnosis information, healthcare specialty information, or patient history information;
  limit the context-relevant content based at least in part on the identity of the user and user preferences associated with the user and stored in the at least one healthcare database;
  transmit the context-relevant content from the healthcare information server to the wireless information device at least part of which is used to automatically generate a presentation to the user via the wireless information device, wherein the presentation comprises the information about the first person, the information about the first room, and the information about the at least one object.

12. The system of claim 11, further comprising a tracking system, in communication with the wireless information device, for identifying the location of the wireless information device.

13. The system of claim 11, wherein the wireless information device is selected from the group of devices consisting of a personal digital assistant, a tablet personal computer, and a mobile telephone.

14. The system of claim 11, wherein the wireless information device is operable to receive information input by the user into the wireless information device.

15. The system of claim 14, wherein the wireless information device is operable to transmit the information input by the user to the server.

16. The system of claim 11, wherein the at least one server is further operable to automatically transmit the context-relevant information, without a request therefor, responsive to ascertaining at least one of the change in the location of the wireless information device.

17. A method for providing context-relevant information in a healthcare facility, comprising:
identifying, by a healthcare information server, a user associated with a wireless information device;
storing information rules in at least one healthcare database, the information rules established at least in part by the user;
receiving, at the healthcare information server, location information identifying the location of the wireless information device;
determining the user's context based at least in part on:
  determining, by the healthcare information server, that the wireless information device is in a first room in the healthcare facility based at least in part on the location information received;
  determining, by the healthcare information server, that a first person is in the same first room at least in part by querying at least one healthcare database based on the identity of the first room;

determining, by the healthcare information server, that a second person is in a second room, wherein the wireless information device is physically closer to the second person than to the first person;

selecting, by the healthcare information server, the first person for retrieving and transmitting information associated therewith by comparing the proximity of the first person and the proximity of the second person to the wireless information device and selecting the first person based upon determining that the first person is in the same first room as the wireless information device; and determining, by the healthcare information server, that at least one object is located in the first room at least in part by querying the at least one healthcare information database based on the identity of the first room and based on an association of the first room with the first person; and transmitting to the wireless information device context-relevant information, wherein the context-relevant content comprises information about the first person, information about the first room, and information about the at least one object, wherein the information about the first person comprises at least one of: medication information, diagnosis information, healthcare specialty information, or patient history information, and wherein the context-relevant information is defined at least in part by the information rules and the user's identity.

18. The method of claim 17, further comprising the step of receiving information input by the user into the wireless information device.

19. The method of claim 17, wherein the step of storing information rules further comprises the step of storing display rules, wherein the display rules establish how the context-relevant information is displayed on the wireless information device.

20. The method of claim 17, wherein the step of identifying the user comprises identifying the user based on a device associated with the user.

21. The method of claim 20, wherein the device associated with the user is selected from a group of devices selected from the group of devices consisting of a smart card, a radio frequency tag, an infrared tag, and a barcode.

22. The method of claim 17, wherein the step of identifying the user comprises identifying the user based on biomedical indicia of the user.

23. The method of claim 17, wherein the information rules identify a plurality of objects about which the user is permitted to receive information, wherein transmitting to the wireless information device context-relevant information further comprises:

selecting context-relevant information from a database, wherein information associated with the plurality of objects identified by the information rules is selected; and transmitting the selected context-relevant information to the wireless information device.

24. The method of claim 23, wherein transmitting to the wireless information device context-relevant information further comprises restricting information not associated with the plurality of objects identified by the information rules from being transmitted.

25. The method of claim 17, wherein determining the user's context further comprises receiving an indication from the wireless information device that the user's context has changed.

26. The method of claim 17, wherein the information rules identify a plurality of patients about whom the user is permitted to receive information, wherein transmitting to the wireless information device context-relevant information further comprises:

selecting context-relevant information from a database, wherein information associated with the plurality of patients identified by the information rules is selected; and transmitting the selected context-relevant information to the wireless information device.

* * * * *

UNITED STATES PATENT AND TRADEMARK OFFICE
CERTIFICATE OF CORRECTION

PATENT NO. : 7,627,334 B2 Page 1 of 1
APPLICATION NO. : 10/768356
DATED : December 1, 2009
INVENTOR(S) : Cohen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1348 days.

Signed and Sealed this

Second Day of November, 2010

David J. Kappos
*Director of the United States Patent and Trademark Office*